United States Patent
Matsuura et al.

(10) Patent No.: US 10,152,576 B2
(45) Date of Patent: Dec. 11, 2018

(54) STORAGE MEDIUM STORING IDENTIFYING HYBRID ORBITAL PROGRAM, IDENTIFYING HYBRID ORBITAL APPARATUS, AND IDENTIFYING HYBRID ORBITAL METHOD

(71) Applicant: FUJITSU LIMITED, Kawasaki-shi, Kanagawa (JP)

(72) Inventors: Azuma Matsuura, Sagamihara (JP); Hiroyuki Sato, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 981 days.

(21) Appl. No.: 14/243,369

(22) Filed: Apr. 2, 2014

(65) Prior Publication Data
US 2014/0336994 A1    Nov. 13, 2014

(30) Foreign Application Priority Data
May 10, 2013    (JP) ................................. 2013-100721

(51) Int. Cl.
   *G06F 19/00*    (2018.01)
(52) U.S. Cl.
   CPC .................................. *G06F 19/701* (2013.01)
(58) Field of Classification Search
   CPC ..................................................... G06F 19/701
   See application file for complete search history.

(56) References Cited

U.S. PATENT DOCUMENTS

| 5,572,439 A | 11/1996 | Nishida et al. |
| 2009/0182514 A1 | 7/2009 | Fujitani et al. |
| 2013/0262054 A1 | 10/2013 | Matsuura et al. |

FOREIGN PATENT DOCUMENTS

| EP | 2 479 695 A2 | 7/2012 |
| JP | 2004-287812 | 10/2004 |
| WO | WO 2008/041304 | 4/2008 |

OTHER PUBLICATIONS

"9.5 Hybrid Orbitals," Jan. 2011, Wayback Machine "http://wps.prenhall.com/wps/media/objects/3311/3391094/blb0905.html", ten pages.*
"Hybridization," Mar. 2008, Wayback Machine "http://courses.chem.psu.edu/chem210/mol-gallery/hybridization/hybrids.html", four pages.*
(Continued)

*Primary Examiner* — Kamini S Shah
*Assistant Examiner* — R. Guill
(74) *Attorney, Agent, or Firm* — Staas & Halsey LLP

(57) ABSTRACT

A storage medium stores an identifying program that causes a computer to execute selecting, from a molecule in a structurally stable state, a second atom and a third atom that combine with a first atom; calculating a first angle between a first straight line passing through the first atom and the selected second atom and a second straight line passing through the first atom and the selected third atom, by referring to a first storage unit in which position information of each atom in the molecule is stored; and identifying a hybrid orbital type of the first atom based on the calculated first angle, by referring to a second storage unit which is stored a condition satisfied by a bond angle formed by the atom and two atoms that combine with the atom being stored in the second storage unit in association with a hybrid atomic orbital type.

18 Claims, 25 Drawing Sheets

(56) References Cited

OTHER PUBLICATIONS

Theodore L. Brown et al., "Chemistry the Central Science,"1994, Prentice-Hall, pp. 305, 307, 309.*
J.P. Foster et al. "Natural Hybrid Orbitals", J. Am. Chem. Soc. 1980, 102, 7211-7218 (1980).
LJ Vujisic et al. "Hybridization in Fulvene and Some Related Cycloalkenes by the Iterative Maximum Overlap Approximation", Journal of Molecular Structure, 33 (1976) 49-62 (1976).
Extended European Search Report dated Oct. 9, 2014 in corresponding European Patent Application No. 14162926.1.
I. Mayer, "Charge, Bond Order and Valence in the AB INITIO SCF Theory," *Chemical Physics Letters*, vol. 97, No. 3, May 1983, pp. 270-274.
W. D. Cornell et al., "A Second Generation Force Field for the Simulation of Proteins, Nucleic Acids, and Organic Molecules," *Journals-American Chemical Society*, vol. 117, No. 19, 1995, pp. 5179-5197.
A. Jakalian et al., "Fast, Efficient Generation of High-Quality Atomic Charges. AM1-BCC Model: II. Parameterization and Validation," *Journal of Computational Chemistry*, vol. 23, No. 16, Oct. 2002, pp. 1623-1641.
J. A. Kalinowski et al., "Class IV Charge Model for the Self-Consistent Charge Density-Functional Tight-Binding Method," *Journal of Physical Chemistry A*, vol. 108, 2004, pp. 2545-2549.
J. Wang et al., "Development and Testing of a General Amber Force Field," *Journal of Computational Chemistry*, vol. 25, No. 9, 2004, pp. 1157-1174.
J. Wang et al., "Automatic atom type and bond type perception in molecular mechanical calculations," *Journal of Molecular Graphics and Modelling*, vol. 25, 2006, pp. 247-260.
H. Fujitani et al., "Massively parallel computation of absolute binding free energy with well equilibrated states," *Physical Review E*, vol. 79, 2009, 12 pages.
European Office Action dated May 10, 2017, in corresponding European Patent Application No. 14 162 926.1.

* cited by examiner

FIG. 4

| | BOND TYPE | ELECTRON DENSITY CONDITION | ATOMIC CONDITION | OTHER CONDITIONS | FORCE FIELD TYPE |
|---|---|---|---|---|---|
| 401-1 | SINGLE BOND | ELECTRON DENSITY < 1.5 | N/A | N/A | AM1BCC CHARGE GAFF FORCE FIELD |
| 401-2 | DOUBLE BOND | 1.5 ≤ ELECTRON DENSITY < 2.5 | N/A | N/A | AM1BCC CHARGE GAFF FORCE FIELD |
| 401-3 | TRIPLE BOND | 2.5 ≤ ELECTRON DENSITY | N/A | N/A | AM1BCC CHARGE GAFF FORCE FIELD |
| 401-4 | COORDINATION BOND | ELECTRON DENSITY < 1.5 | NITROGEN ATOM AND OXYGEN ATOM (N-OXIDE), NITROGEN ATOM AND SULFUR ATOM (N-SULFIDE), OR, ... | N/A | AM1BCC CHARGE |
| 401-5 | AROMATIC BOND | PRESENCE OF BOND | TYPE OF SIX ATOMS IS ANY OF CARBON ATOM, NITROGEN ATOM, ..., DICATIONIC SULFUR ATOM; BOND TYPE OF TWO ADJACENT ATOMS OF SIX ATOMS IS AROMATIC BOND IN SIX-MEMBERED RING AND TYPE OF OTHER FOUR ATOMS IS ANY OF CARBON ATOM, NITROGEN ATOM, ..., DICATIONIC SULFUR ATOM; OR ... | TYPE OF BOND WITH ATOM THAT COMBINES WITH RING IS SINGLE BOND OR COORDINATION BOND | AM1BCC CHARGE GAFF FORCE FIELD |
| 401-6 | DELOCALIZED BOND | PRESENCE OF BOND | NITROGEN ATOM AND OXYGEN ATOM OF NITRO GROUP; CARBON ATOM AND OXYGEN ATOM OF CARBOXYLATE ION; PHOSPHORUS ATOM AND OXYGEN ATOM OF PHOSPHATE ION; SULFUR ATOM AND OXYGEN ATOM OF SULFONATE ION; OR ... | N/A | AM1BCC CHARGE |

| COORDINATION NUMBER | 1 | 2 | 3 | 4 |
|---|---|---|---|---|
| CATION (QUADRIVALENT) | N/A | N≡N⁺—  /  —N⁺≡C—  /  =N⁺=C<   sp  [25] | >N⁺=   sp² [23] | >N⁺<   sp³ [21] |
| NEUTRAL (TRIVALENT) | N≡C— [25] | —N=C<   sp² [24] | >N—   sp³ [21]/[22]/[23] | N/A |
| ANION (DIVALENT) | N⁻=C< [25] | —N⁻—C<   sp³ [21]/[22]/[23] | N/A | N/A |
| BOND TYPE | DOUBLE BOND TRIPLE BOND | SINGLE BOND DOUBLE BOND TRIPLE BOND, AND SO ON | SINGLE BOND DOUBLE BOND, AND SO ON | SINGLE BOND, AND SO ON |

701

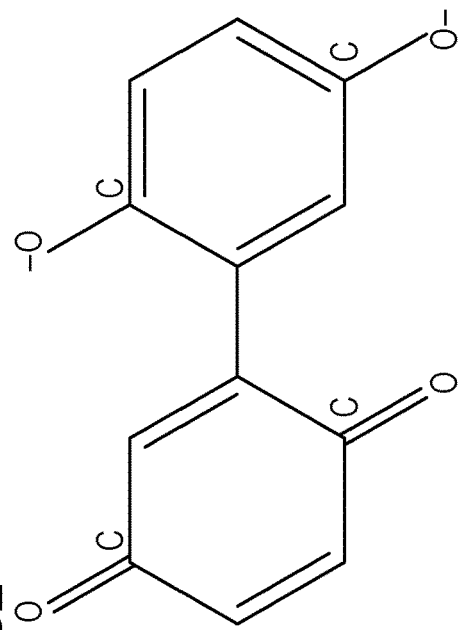
FIG. 10B2
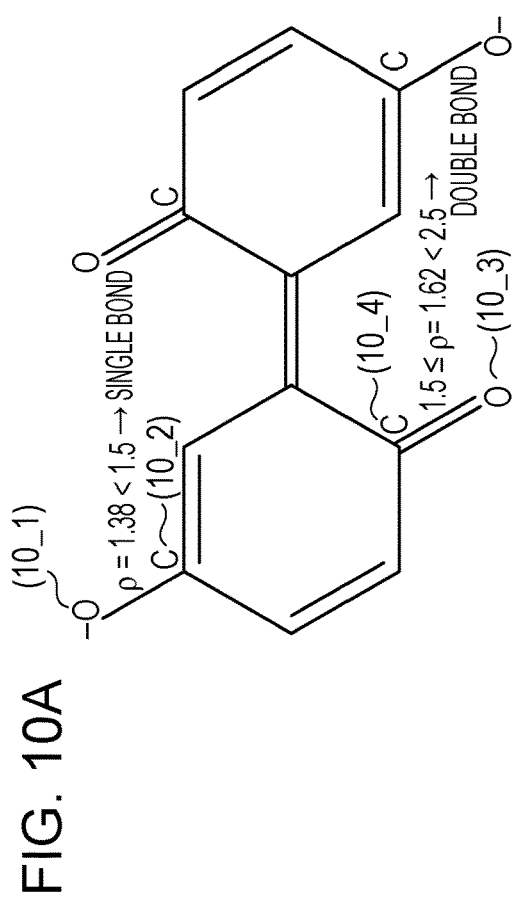
FIG. 10A
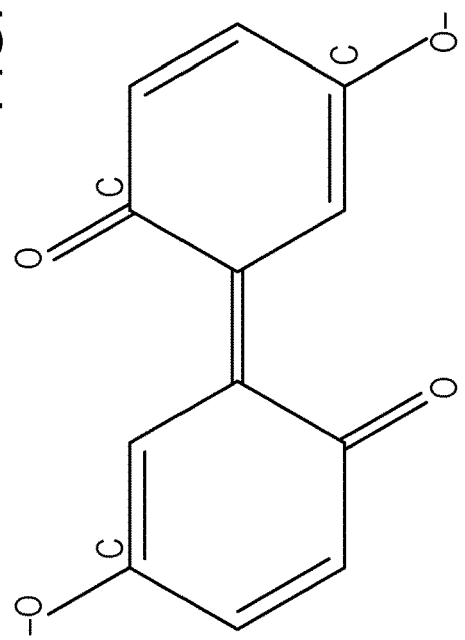
FIG. 10B1

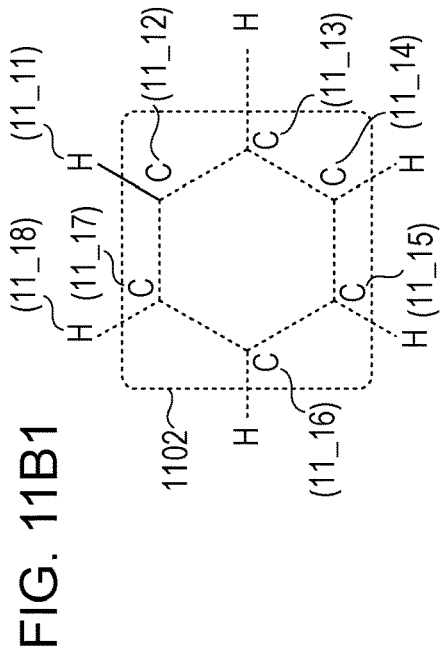
FIG. 11A1
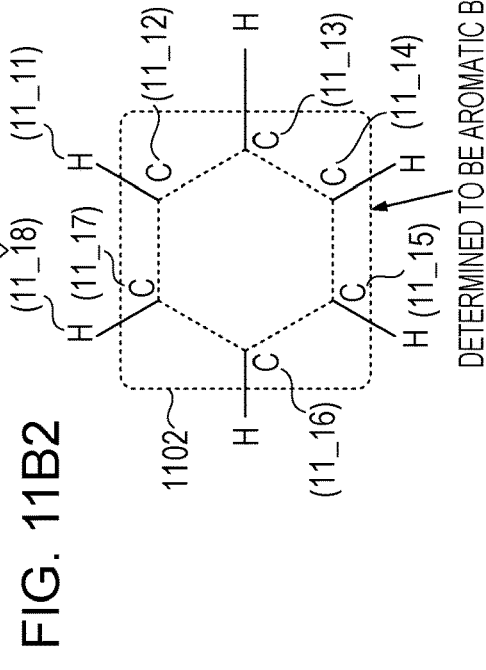
FIG. 11B1
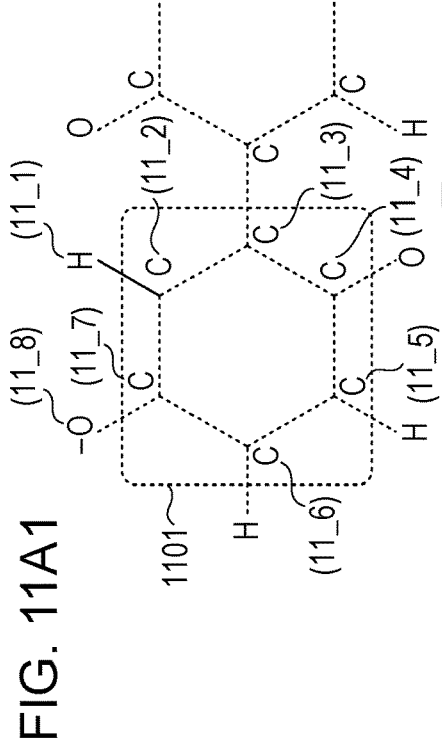
FIG. 11A2
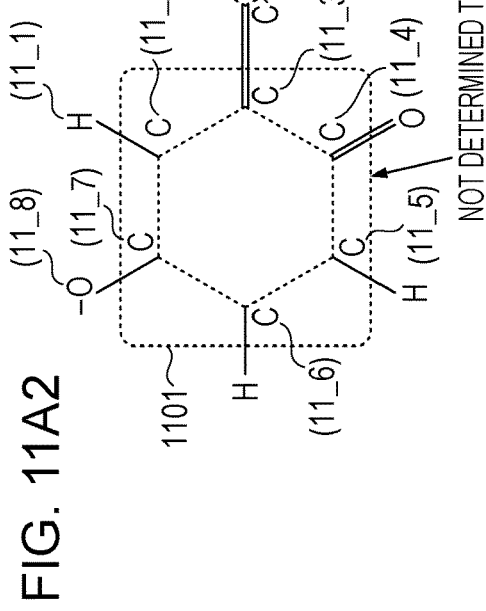
FIG. 11B2

BOND PARAMETER (1801)

| | Rk | Req |
|---|---|---|
| [c] – [c] | 290.1 | 1.55 |
| [c] – [c1] | 379.8 | 1.46 |
| [c] – [c2] | 449.9 | 1.406 |
| [c] – [c3] | 328.3 | 1.508 |
| [c] – [ca] | 349.7 | 1.487 |
| ... | ... | ... |

BOND-ANGLE PARAMETER (1802)

| | Tk | Teq |
|---|---|---|
| [c] – [c] – [c3] | 61.7 | 116.86 |
| [c] – [c] – [cc] | 64 | 111.67 |
| [c] – [c] – [cd] | 64 | 111.67 |
| [c] – [c] – [ha] | 44.8 | 115.43 |
| ... | ... | ... |

DIHEDRAL PARAMETER (1803)

| | Pk | p | n |
|---|---|---|---|
| [n] – [c3] – [c] – [n] | 1.7 | 180 | −1 |
| [n] – [c3] – [c] – [n] | 2 | 180 | 2 |
| [c] – [n] – [c] – [c] | 0.85 | 180 | −2 |
| [c] – [n] – [c3] – [c] | 0.8 | 0 | 1 |
| ... | ... | ... | ... |

NON-BOND PARAMETER (1804)

| | vdw | wd |
|---|---|---|
| [c] | 1.908 | 0.086 |
| [c1] | 1.908 | 0.086 |
| [c2] | 1.908 | 0.086 |
| [c3] | 1.908 | 0.1094 |
| [ca] | 1.908 | 0.086 |
| ... | ... | ... |

$$E = \sum_{bonds} k_r(r - r_{eq})^2 + \sum_{angles} k_\theta(\theta - \theta_{eq})^2$$

Rk, Req (bonds); Tk, Teq (angles)

$$+ \sum_{dihedrals} \sum_n \frac{1}{2} v_n [1 + \cos(n\varphi - \gamma)]$$

Pk, n, p $$+ \sum_{i<j} 4\varepsilon_{ij}\left[\left(\frac{\sigma_{ij}}{r_{ij}}\right)^{12} - \left(\frac{\sigma_{ij}}{r_{ij}}\right)^6\right] + \sum_{i<j} \frac{q_i q_j}{r_{ij}} \quad \cdots (5)$$

wd, vdw (non-bonds); charges

STORAGE MEDIUM STORING IDENTIFYING HYBRID ORBITAL PROGRAM, IDENTIFYING HYBRID ORBITAL APPARATUS, AND IDENTIFYING HYBRID ORBITAL METHOD

CROSS-REFERENCE TO RELATED APPLICATION

This application is based upon and claims the benefit of priority of the prior Japanese Patent Application No. 2013-100721 filed on May 10, 2013, the entire contents of which are incorporated herein by reference.

FIELD

The embodiment discussed herein is related to a storage medium storing an identifying program, an identifying apparatus, and an identifying method.

BACKGROUND

Heretofore, technologies for determining molecule structures of molecules have become available. There is also a related technology for a method that assigns a molecular force field to a molecule. According to the technology, a bond type representing the type of bond between atoms is determined depending on whether or not the bond distance between atoms which is calculated using quantum-mechanical-calculation called a molecular orbital method exceeds a predetermined threshold (For example, see International Publication Pamphlet No. WO 2008/041304).

According to the related art, however, it is difficult to assign an appropriate molecular force field to a molecule. For example, when the bond type is determined based on the bond distance between atoms, the difference in the bond distance between the atoms, the difference being caused by a difference in the bond type, is small. Thus, when the calculation accuracy of the quantum-mechanical-calculation is low, there are cases in which an erroneous bond type is determined and the erroneous bond type may cause assignment of an erroneous molecular force field.

SUMMARY

According to an aspect of the embodiments, a storage medium stores an identifying program that causes a computer to execute selecting, from a molecule in a structurally stable state, a second atom and a third atom that combine with a first atom; calculating a first angle between a first straight line passing through the first atom and the selected second atom and a second straight line passing through the first atom and the selected third atom, by referring to a first storage unit in which position information of each atom in the molecule is stored; and identifying a hybrid orbital type of the first atom based on the calculated first angle, by referring to a second storage unit which is stored a condition satisfied by a bond angle formed by the atom and two atoms that combine with the atom being stored in the second storage unit in association with a hybrid atomic orbital type.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 4 illustrates an example of the contents stored in an electron-density-based bond-type determination condition table;

FIG. 7 illustrates an example of atomic species and bond types of nitrogen atoms;

FIGS. 10A, 10B1, and 10B2 are diagrams illustrating examples of a method for atomic-species determination based on electron densities;

FIGS. 11A1, 11A2, 11B1, and 11B2 are diagrams illustrating examples of a method for aromatic-bond determination based on electron densities;

FIGS. 18A to 18D illustrate an example of a force field table;

FIG. 19 illustrates an example of a molecular force-field function;

DESCRIPTION OF EMBODIMENT

An identifying program, an identifying apparatus, and an identifying method according to an embodiment disclosed herein will be described below with reference to the accompanying drawings.

Figure 1:
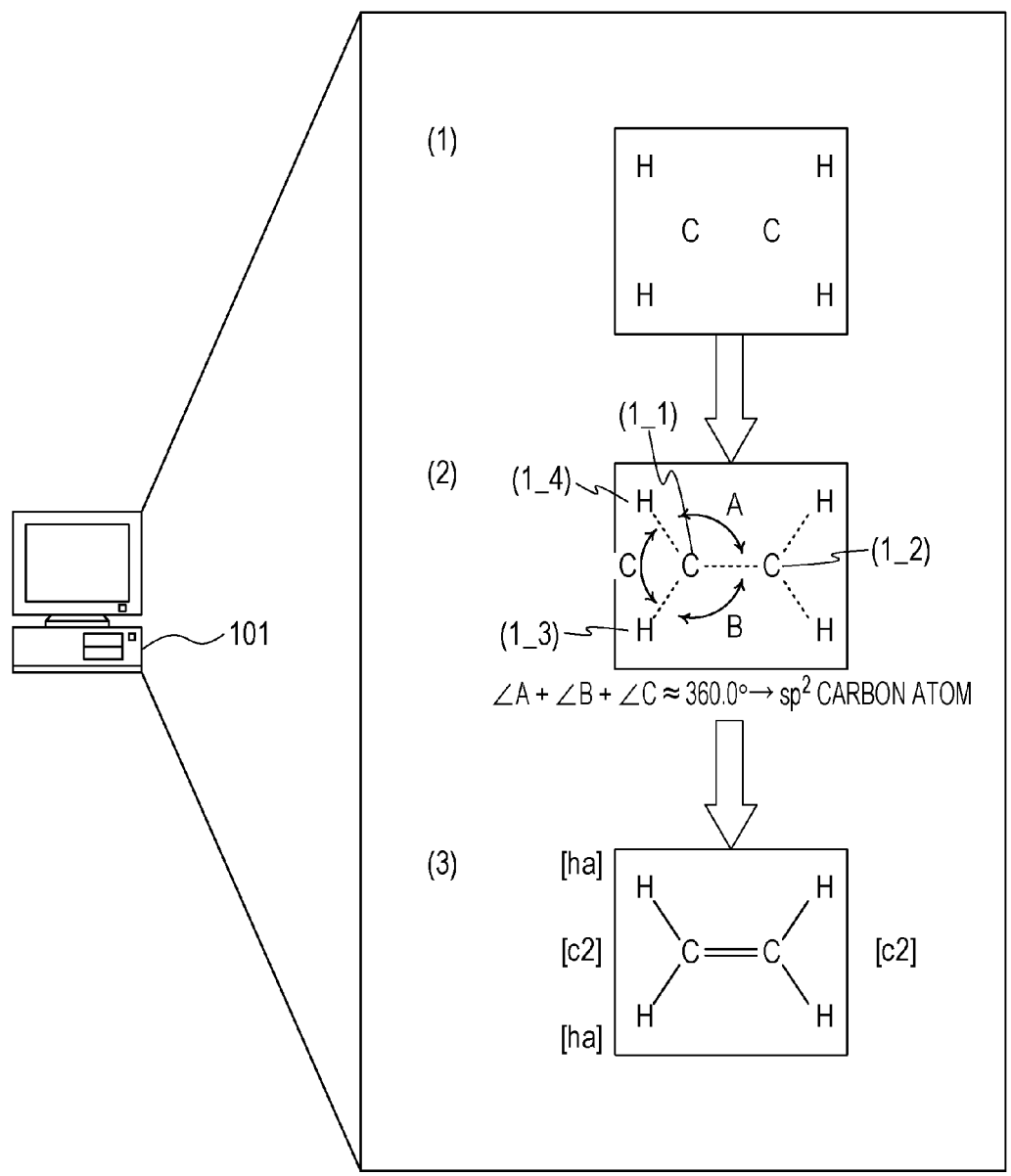
FIG. 1 is a block diagram illustrating an example of an operation of an identifying apparatus according to the present embodiment.

FIG. 1 is a block diagram illustrating an example of an operation of an identifying apparatus according to the present embodiment. An example operation of an identifying apparatus 101 that determines atomic species of atoms and assigns a molecular force field will be described with reference to FIG. 1. For performing simulation of a new molecule or molecular assembly, the identifying apparatus 101 performs processing for helping to decide what molecular force field is to be assigned. The molecule may be a single molecule composed of the same type of atoms or may be a compound composed of multiple types of atoms. Defining a molecular force field makes it possible to perform simulation of the geometric structure, electronic properties, parameters, and so on of a molecule. For example, in the field of drug discovery, by utilizing molecular force fields, a simulation apparatus can simulate how a drug candidate substance reacts with known proteins that constitute the human body or viruses.

When the assignment of the molecular force field is not appropriate, the result of the simulation becomes less accurate and becomes significantly different from the reality. A molecular force field can be uniquely identified based on atomic species. Thus, the identifying apparatus 101 according to the present embodiment is adapted to assign an appropriate molecular force field by determining appropriate atomic species.

The atomic species of atoms is information identified by the type of a target atom and a difference in the bonding state of atoms. Types of molecular force field include, for example, a force field related to an electrostatic interaction energy, and a more detailed definition is described in Araz Jakalian, and two others, "Fast, Efficient Generation of High-Quality Atomic Charges. AM1-BCC Model: II. Parameterization and Validation", *Journal of Computational Chemistry*, Vol. 23, pp. 1623-1641, 2002. A force field related to the electrostatic interaction energy will hereinafter be referred to as "AM1BCC charge". An atomic species related to the electrostatic interaction energy will also be referred to as an "AM1BCC atomic species". The AM1BCC atomic species is also described in the literature by Araz Jakalian, et al.

One example of force fields other than the AM1BCC charge is a general Amber force field (GAFF). When the GAFF atomic species are determined in the GAFF force field, a molecular force field can be uniquely assigned. The GAFF force field is described in Junmei Wang, and four others, "Development and Testing of a General Amber Force Field", *Journal of Computational Chemistry*, Vol. 25, pp. 1157-1174, 2004). A force field corresponding to the GAFF atomic species is described in Wendy D. Cornell, and nine others, "A Second Generation Force Field for the Simulation of Proteins, Nucleic Acids, and Organic Molecules", *Journals-American Chemical Society*, Vol. 117, pp. 5179-5197, 1995.

Next, a description will be given of first to third methods for determining an atomic species. The first method for determining an atomic species employs a method for determining a type of bond by using valences. By using valences to determine a bond type representing the type of a bond that combines two atoms, an apparatus that executes the first method can uniquely determine an atomic species based on the bond type and thus can determine the atomic species corresponding to the bond type. The types of bond are defined by, for example, a force field related to an electrostatic interaction energy, and are classified into, for example, a single bond, a double bond, a triple bond, an aromatic bond, a coordination bond, and a delocalized bond.

With the first method, however, there are cases in which ambiguity remains in the assignment of the bond types, and a molecular force field that is different from reality is assigned. More specifically, nitrogen atoms have one-fold coordination to four-fold coordination, and the atoms have three types of state, namely, a cationic state, a neutral state, and an anionic state, and bond types that are derived from these states include a single bond, a double bond, a triple bond, an aromatic bond, a coordination bond, a delocalized bond, and so on. Hence, the number of selectable bond types is enormous. A target molecule to be simulated may include several tens or several hundreds of atoms, in which case, the amount of processing increases exponentially.

The second method for determining an atomic species employs a method for determining a bond type based on a bond distance between atoms by using quantum-mechanical-calculation. More specifically, an apparatus that executes the second method calculates a distance between atoms and compares the distance with a predetermined threshold to determine a bond type.

With the second method, however, the value of the threshold varies depending on the quantum-mechanical-calculation scheme. For example, when the apparatus that executes the second method applies a threshold determined by a quantum-mechanical-calculation scheme A to a molecular structure calculated by a quantum-mechanical-calculation scheme B, an erroneous bond type may be assigned.

The third method for determining an atomic species employs a method for determining a bond type based on an electron density between atoms by using quantum-mechanical-calculation. More specifically, the apparatus that executes the third method calculates an electron density between atoms and compares the electron density with a predetermined threshold to determine a bond type.

The electron density will now be described in more detail. The apparatus that executes the third method determines an electron density between two atoms by using the method of Mulliken or Loewdin. The apparatus that executes the third method may use a bond order as the electron density. For example, the apparatus that executes the third method may use the Mayer bond order or the Coulson bond order. The Mayer bond order is detailed in I Mayer, "Charge, Bond Order and Valence in the AB Initio SCF Theory", *Chemical Physics Letters*, Vol. 97, pp. 270-274, 1983.

The Mayer bond order gives values of about 1, 1.5, 2, and 3 for the single bond, conjugated bond, double bond, and triple bond types, respectively. In the absence of bonds, the Mayer bond order indicates substantially zero. Details are described in Jaroslaw A. Kalinowski, and four others, "Class IV Charge Model for the Self-Consistent Charge Density-Functional Tight-Binding Method", *Journal of Physical Chemistry A*, Vol. 108, pp. 2545-2549, 2004.

With the third method, however, a functional group having electron donation or electron acceptability combines with a molecule having a conjugated system. Thus, when electrons move in the molecule, there are cases in which it is significantly difficult to identify the bond type.

Accordingly, by utilizing the fact that the bond angle increases according to the hybrid atomic orbital, the identifying apparatus 101 according to the present embodiment identifies a hybrid atomic orbital, based on bond angles obtained by quantum-mechanical-calculation. Thus, the identifying apparatus 101 can identify a hybrid orbital with high accuracy even when the calculation accuracy of the quantum-mechanical-calculation is low and can improve the accuracy of assigning a molecular force field.

Atoms depicted with parenthesized reference numerals in FIGS. 1 to 25 will hereinafter be represented by "atom_ (reference numeral)", for convenience of illustration. For example, when a hydrogen atom "H" is given reference numeral "(1)", it is represented as H_(1) in FIGS. 1 to 25. In FIGS. 1 to 25, atomic species are depicted by characters in brackets, for convenience of illustration.

It is assumed that, as illustrated at (1) in FIG. 1, the three-dimensional structure of an ethylene molecule $C_2H_4$ is given to the identifying apparatus 101 as a target molecule. The three-dimensional structure is an energetically stable structure determined by quantum-mechanical-calculation, such as a molecular orbital method, a density functional method, or a valence bond method.

Next, as illustrated at (2) in FIG. 1, the identifying apparatus 101 selects a second atom and a third atom that combines with a first atom selected from the ethylene molecule. In addition, when three atoms combine with the first atom, the identifying apparatus 101 may further select, from the molecule, a fourth atom that combines with the first atom. In this case, the identifying apparatus 101 selects, as the atoms that combine with the first atom, atoms that are within a distance defined by a covalent radius, an ionic radius, the van der Waals radius, or the like. In the example at (2) in FIG. 1, the first atom is represented by C_(1_1), the second atom is represented by C_(1_2), the third atom is represented by H_(1_3), and the fourth atom is represented by H_(1_4).

By referring to a first storage unit in which position information of atoms in the molecule is stored, the identifying apparatus 101 calculates a first angle between a first straight line passing through the first atom and the second atom and a second straight line passing through the first atom and the selected third atom. The first storage unit stores therein the position information of atoms in a molecule having an energetically stable structure. Although two straight lines form two angles, that is, an angle of 180° or less and an angle of 180° or more, the identifying apparatus 101 calculates an angle that is 180° or less.

At (2) in FIG. 1, the first angle corresponds to ∠A. In addition, when the fourth atom is selected, the identifying apparatus 101 may determine a second angle between the first straight line and a third straight line passing through the first atom and the fourth atom and a third angle between the second straight line and the third straight line. At (2) in FIG. 1, the second angle corresponds to ∠B. At (2) in FIG. 1, the third angle corresponds to ∠C. A cosine formula may be used to determine the angles by using the position information of the atoms.

After calculating the angles, the identifying apparatus 101 identifies the hybrid orbital type of the first atom by referring to a second storage unit and based on the calculated first angle. Conditions satisfied by a bond angle defined by an atom and two atoms that combine with the atom are stored in the second storage unit in association with hybrid atomic orbital types. When the fourth atom is selected, the identifying apparatus 101 may also identify the hybrid orbital type of the first atom by referring to the second storage unit and based on the sum of the first angle, the second angle, and third angle.

Figure 3:
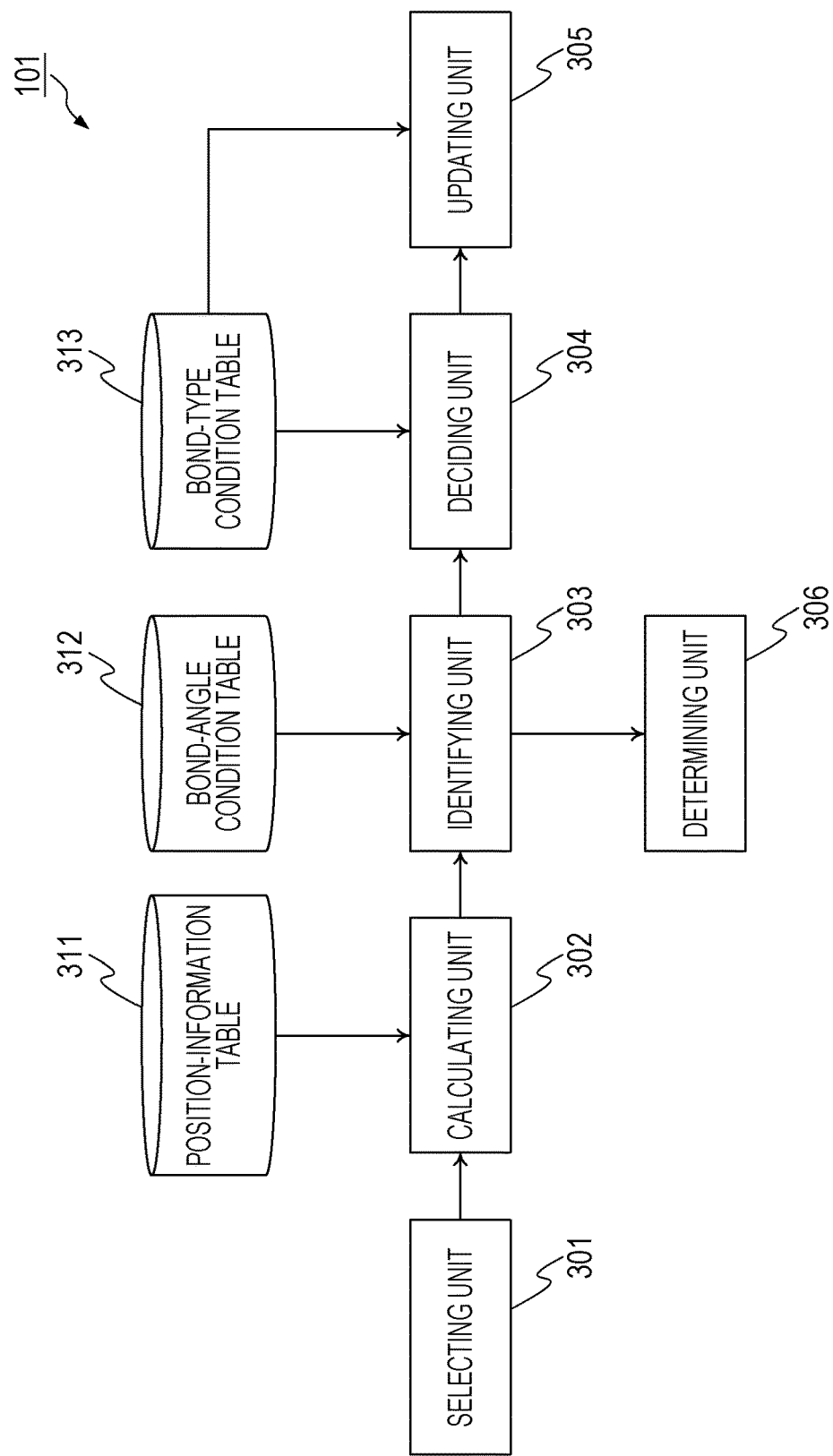
FIG. 3 is a block diagram illustrating an example of the functional configuration of the identifying apparatus.

The second storage unit is described later with reference to FIGS. 3 and 5. The bond angle refers to an angle that is 180° or less out of angles centered on a certain atom and formed between a straight line passing through the certain atom and one of two atoms that combine with the certain atom and a straight line passing through the certain atom and the other atom. The bond angle formed by a straight line passing through a first atom and a second atom and a straight line passing through the first atom and a third atom, the second atom and the third atom combining with the first atom, may be referred to as a bond angle "second-atom_ first-atom_third-atom".

The hybrid orbital is a method introduced to explain chemical bonds of atoms, and refers to an orbital when an s orbital and a p orbital, among the electron orbitals, mix with each other to produce a type of bond. Mixing of one s orbital and one p orbital yields an sp orbit, mixing of one s orbital and two p orbitals yields an $sp^2$ orbital, and mixing of one s orbital and three p orbitals yields an $sp^3$ orbital.

An atom whose hybrid orbital type is sp may be hereinafter referred to as an "sp atom". An atom whose hybrid orbital type is $sp^2$ may be referred to as an "$sp^2$ atom". In addition, an atom whose hybrid orbital type is $sp^3$ may be referred to as an "$sp^3$ atom". For example, a carbon atom whose hybrid orbital type is sp is referred to as an "sp carbon atom".

In the example in FIG. 1, ∠A+∠B+∠C is in the vicinity of 360°, and this satisfies a condition for an $sp^2$ atom. Thus, the identifying apparatus 101 determines that C_(1_1) is an $sp^2$ carbon atom.

Subsequently, as illustrated at (3) in FIG. 1, the identifying apparatus 101 determines the atomic species of the first atom, based on the hybrid orbital type of the first atom and the atomic species of each of the atoms that combine with the first atom. More specifically, when an AM1BCC force field is assigned, the identifying apparatus 101 stores therein Table 1 in the literature by Araz Jakalian et al., and when a GAFF force field is assigned, stores Table 1 in the literature by Junmei Wang, et al. By referring to the corresponding one of the tables, the identifying apparatus 101 determines the atomic species of the first atom, the atomic species corresponding to the hybrid orbital type and the atomic species of each of the atoms that combine with the first atom.

In the example in FIG. 1, the GAFF atomic species of C_(1_2) is [c2] ($sp^2$ carbon), and the GAFF atomic species of H_(1_3) and H_(1_4) are both hydrogens on aromatic carbon [ha]. In this case, it is assumed that the GAFF atomic species of C_(1_2) and the GAFF atomic species of H_(1_3) and H_(1_4) have been determined using any of the first to third methods for atomic-species determination. The GAFF atomic species [ha] indicates that the atom in question is a hydrogen atom that combines with an sp carbon atom or an $sp^2$ carbon atom. By referring to Table 1 in the literature by Junmei Wang, et al., the identifying apparatus 101 determines that C_(1_1) is an $sp^2$ carbon atom, C_(1_2) is not an aromatic carbon, and the atoms that combine with C_(1_1) are neither oxygen atoms nor sulfur atoms. Thus, the identifying apparatus 101 determines that the GAFF atomic species of C_(1_1) is [c2]. The identifying apparatus 101 will be described below with reference to FIGS. 2 to 25.

(Hardware of Identifying Apparatus)

Figure 2:
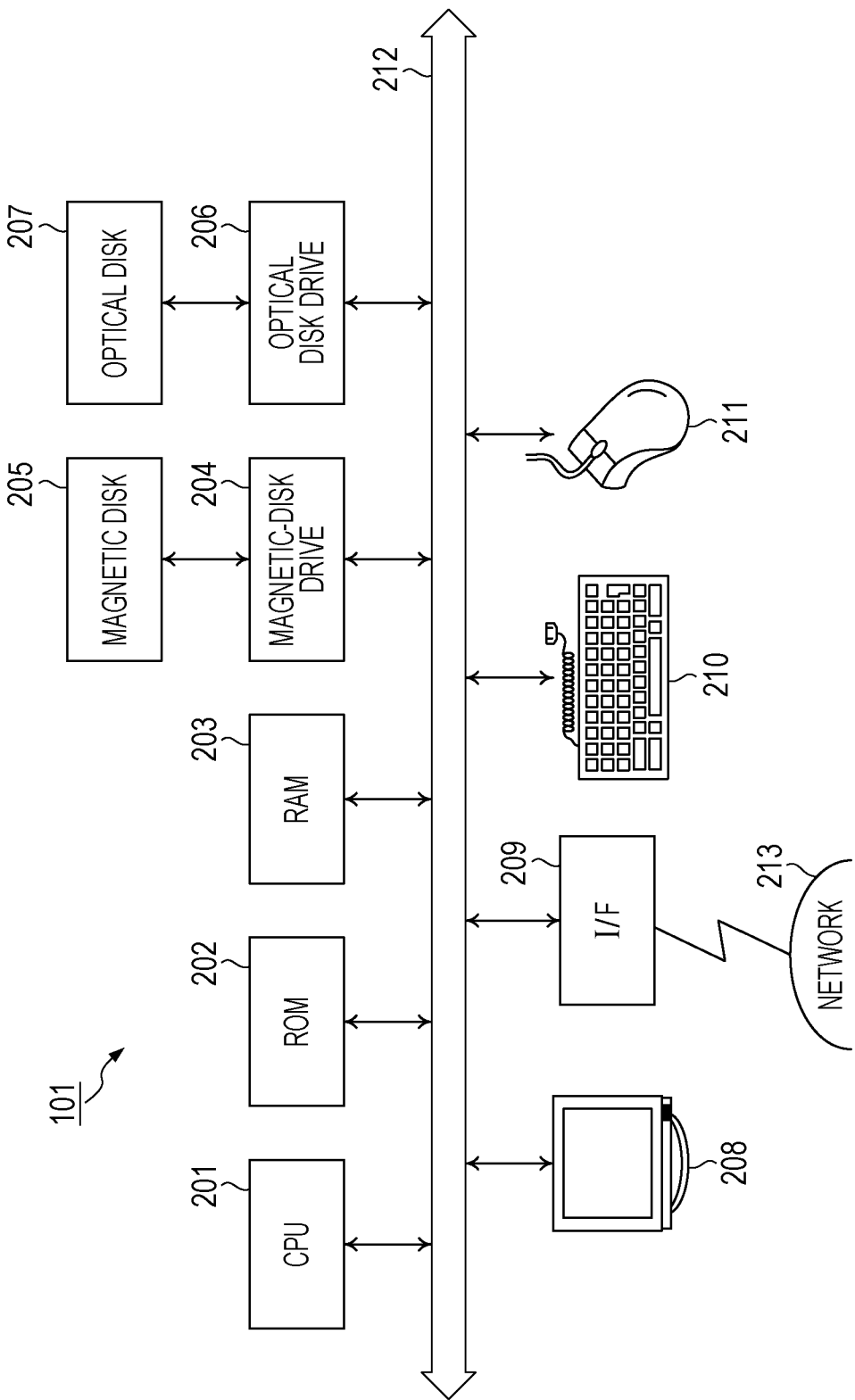
FIG. 2 is a block diagram illustrating an example of the hardware configuration of the identifying apparatus.

FIG. 2 is a block diagram illustrating an example of the hardware configuration of the identifying apparatus 101. As illustrated in FIG. 2, the identifying apparatus 101 includes a central processing unit (CPU) 201, a read only memory (ROM) 202, and a random access memory (RAM) 203. The identifying apparatus 101 also includes a magnetic-disk drive 204, a magnetic disk 205, an optical disk drive 206, and an optical disk 207, which serve as storage devices. The identifying apparatus 101 further includes a display 208, an interface (I/F) 209, a keyboard 210, and a mouse 211, which serve as input/output devices for the user or for equipment other than the identifying apparatus 101. These elements are inter-connected through a bus 212.

In this case, the CPU 201 is a computational processing device that is responsible for controlling the entire identifying apparatus 101. The ROM 202 is a nonvolatile memory that stores therein programs, such as a boot program. The RAM 203 is a volatile memory used as a work area for the CPU 201. The magnetic-disk drive 204 is a control device for controlling writing/reading data to/from the magnetic disk 205 under the control of the CPU 201. The magnetic disk 205 is a nonvolatile storage medium that stores thereon data written under the control of the magnetic-disk drive 204. The identifying apparatus 101 may also have a solid-state drive.

The optical disk drive 206 is a control device for controlling writing/reading data to/from the optical disk 207 under the control of the CPU 201. The optical disk 207 is a nonvolatile recording medium that stores thereon data written under the control of the optical disk drive 206. The optical disk 207 also causes a computer to read data stored in the optical disk 207.

The display 208 is a display device that displays a cursor, icons and a toolbox, as well as data, such as a document, an image, and function information. For example, the display 208 may be implemented by a cathode ray tube (CRT) display, a thin-film transistor (TFT) liquid-crystal display, a plasma display, or the like.

The I/F 209 is a control device that is responsible for interfacing between the inside of the identifying apparatus 101 and a network 213 to control outputting/inputting data to/from an external apparatus. The I/F 209 is connected with the network 213, such as a local area network (LAN), a wide area network (WAN), and/or the Internet, through a communication channel, and is connected with another apparatus through the network 213. The I/F 209 may be implemented by, for example, a modem or a LAN adapter.

The keyboard 210 is a device having keys for inputting characters, numerals, and various instructions to input data. The keyboard 210 may also be a touch-panel input pad, a numeric keypad, or the like. The mouse 211 is a device for moving a cursor, selecting a range, or moving or resizing a window. Instead of the mouse 211, the identifying apparatus 101 may also have any device that serves as a pointing device. Examples include a trackball and a joystick.

(Example of Functional Configuration of Identifying Apparatus 101)

Next, a description will be given of an example of the functional configuration of the identifying apparatus 101. FIG. 3 is a block diagram illustrating an example of the functional configuration of the identifying apparatus 101. The identifying apparatus 101 includes a selecting unit 301, a calculating unit 302, an identifying unit 303, a deciding unit 304, an updating unit 305, and a determining unit 306. The selecting unit 301, the calculating unit 302, the identifying unit 303, the deciding unit 304, the updating unit 305, and the determining unit 306 serve as control units, and the CPU 201 executes a program stored in a storage device to thereby realize the functions thereof. Specific examples of the storage device include the ROM 202, the RAM 203, the magnetic disk 205, and the optical disk 207 illustrated in FIG. 2. Alternatively, another CPU may execute the program via the I/F 209 to realize the functions of the selecting unit 301, the calculating unit 302, the identifying unit 303, the deciding unit 304, the updating unit 305, and the determining unit 306.

The identifying apparatus 101 is also capable of accessing a position-information table 311, a bond-angle condition table 312, and a bond-type condition table 313. The position-information table 311, the bond-angle condition table 312, and the bond-type condition table 313 are stored in a storage device, such as the RAM 203, the magnetic disk 205, and/or the optical disk 207. In order to execute a method for bond-type determination based on electron densities, the identifying apparatus 101 according to the present embodiment is capable of accessing quantum-mechanical-calculation results and an electron-density-based bond-type determination condition table, which are not illustrated in FIG. 3. The quantum-mechanical-calculation results and the electron-density-based bond-type determination condition table are stored in a storage device, such as the RAM 203, the magnetic disk 205, and/or the optical disk 207.

The quantum-mechanical-calculation results include the electron density of electrons belonging to each of the atoms in a molecule in a structurally stable state and the degree of atomic orbital overlap between the atoms in the molecule. The electron density of electrons belonging to each of the atoms in a molecule in a structurally stable state may be represented by, for example, an electron density matrix. The degree of atomic orbital overlap between the atoms in the molecule may also be represented by, for example, an overlap integral matrix. The electron density matrix and the overlap integral matrix are described later with reference to FIGS. 9A to 9C.

In the electron-density-based bond-type determination condition table, bond types representing the types of bonds between atoms and conditions for electron densities between atoms that combine via the bond types are stored in association with each other. The electron-density-based bond-type determination condition table is described later with reference to FIG. 4.

The position-information table 311 stores therein position information of each of the atoms in a molecule in a structurally stable state. More specifically, when the molecule is an ethylene molecule, the position-information table 311 stores therein position information of two carbon atoms in an XYZ space and position information of four hydrogen atoms in the XYZ space.

In the bond-angle condition table 312, conditions satisfied by a bond angle formed by a certain atom and two atoms that combine with the certain atom are stored in association with hybrid atomic orbital types. The bond-angle condition table 312 corresponds to the second storage unit described above with reference to FIG. 1.

In the bond-angle condition table 312, conditions satisfied by the sum of bond angles formed by a certain atom and two atoms selected from three atoms that combine with the certain atom may also be stored in association with the hybrid atomic orbital types.

In the bond-type condition table 313, conditions satisfied by a bond type representing a bond between a certain atom and other atoms that combine with the certain atom are stored in association with hybrid atomic orbital types. The bond-angle condition table 312 and the bond-type condition table 313 may be a single table obtained by combining the two tables. Details of the bond-type condition table 313 are described later with reference to FIG. 6.

The selecting unit 301 selects, from a molecule in a structurally stable state, a second atom and a third atom that combine with a first atom. When three atoms combine with the first atom, the selecting unit 301 may further select, from the molecule, a fourth atom that combines with the first atom. The identification information of the selected atoms is stored in a storage area in the RAM 203, the magnetic disk 205, the optical disk 207, or the like.

By referring to the position-information table 311, the calculating unit 302 calculates a first angle between a first straight line passing through the first atom and the second atom selected by the selecting unit 301 and a second straight line passing through the first atom and the third atom selected by the selecting unit 301. As a specific example of calculating the first angle, the calculating unit 302 assumes a triangle whose vertices correspond to the first atom, the second atom, and the third atom. The calculating unit 302 then calculates a first angle by applying a cosine formula to the side between the first atom and the second atom, the side between the first atom and the third atom, the side between the second atom and the third atom, and the first angle. By referring to the position-information table 311, the calculating unit 302 may further calculate a second angle between the first straight line and a third straight line passing through the first atom and a fourth atom selected by the selecting unit 301 and a third angle between the second straight line and the third straight line. The determined angle values are stored in a storage area in the RAM 203, the magnetic disk 205, the optical disk 207, or the like.

By referring to the bond-angle condition table 312, the identifying unit 303 identifies the hybrid orbital type of the first atom, based on the first angle calculated by the calculating unit 302. By referring to the bond-angle condition table 312, the identifying unit 303 may also identify the hybrid orbital type of the first atom, based on the first angle, the second angle calculated by the calculating unit 302, and the third angle calculated by the calculating unit 302. In this case, since the bond angle is an angle of 180° or less out of the angles between the straight lines, the condition stored in the bond-angle condition table 312 is also a condition that is satisfied by an angle of 180° or less out of the angles between the straight lines. In this case, the bond angle may be an angle of 180° or more out of the angles between the straight lines, and the condition stored in the bond-angle condition table 312 may also be a condition that is satisfied by an angle of 180° or more out of the angles between the straight lines. A specific example of identifying the hybrid orbital type is described later with reference to FIG. 5. The identified hybrid orbital type is stored in a storage area in the RAM 203, the magnetic disk 205, the optical disk 207, or the like.

By referring to the bond-type condition table 313, the deciding unit 304 decides whether or not the type of bond between the first atom and each of the atoms that combine with the first atom satisfies a condition for the hybrid orbital type of the first atom, the type being identified by the identifying unit 303. The type of bond may also be a bond type determined using valences, may also be a bond type determined based on the bond distance between atoms, and may also be a bond type determined based on the electron density between atoms.

For example, when the hybrid orbital type of the first atom, the type being identified by the identifying unit 303, is $sp^3$ and all of the bond types are single bonds, the deciding unit 304 decides that the condition is satisfied. The result of the decision is stored in a storage area in the RAM 203, the magnetic disk 205, the optical disk 207, or the like.

It is now assumed that the deciding unit 304 decides that the types of bonds between the first atom and the atoms do not satisfy the condition for the hybrid orbital type of the first atom. In this case, the updating unit 305 updates the types of bonds between the first atom and the atoms, based on the condition for the hybrid orbital type of the first atom and a result of comparison of the distances or the electron densities between the first atom and the atoms. Specific examples of the update are described later with reference to FIGS. 17A to 17C.

The determining unit 306 determines the atomic species of the first atom, based on the hybrid orbital type of the first atom, the type being identified by the identifying unit 303, and the atomic species of each of the atoms that combine with the first atom. A specific method for the determination is analogous to that described above with reference to FIG. 1. The result of the determination is stored in a storage area in the RAM 203, the magnetic disk 205, the optical disk 207, or the like.

FIG. 4 illustrates an example of the contents stored in the electron-density-based bond-type determination condition table. A bond-type determination condition table 401 stores therein records 401-1 to 401-6 for respective bond types. The bond-type determination condition table 401 has five fields, that is, a "bond type" field, an "electron density condition" field, an "atomic condition" field, an "other conditions" field, and a "force field type" field. Identification information indicating a type of bond is stored in the "bond type" field. A condition regarding an electron density between atoms that combine via the corresponding bond type is stored in the "electron density condition" field. The types of atoms that combine via the corresponding bond type are stored in the "atomic condition" field. Conditions other than the electron density condition and the atomic condition are stored in the "other conditions" field. A force field type that defines an atomic species is stored in the "force field type" field.

For example, the record 401-1 indicates that the electron density is less than 1.5 as a condition for a single bond. The record 401-1 also indicates that a single bond is defined together with an AM1BCC charge and a GAFF force field. The contents of the "electron density condition" field in the record 401-1 indicate a first condition based on the electron density.

Similarly, the contents of the "electron density condition" field in the record 401-2 indicate a second condition based on the electron density, and the contents of the "electron density condition" field in the record 401-3 indicate a third condition based on the electron density. The contents of the "electron density condition" field in the record 401-4 indicate a fourth condition based on the electron density. In addition, the contents of the "atomic condition" field in the record 401-4 indicate a fifth condition based on the electron density. The contents of the "atomic condition" field in the record 401-5 indicate a sixth condition based on the electron density. Details of the sixth condition based on the electron density are detailed in FIG. 1a in the literature by Araz Jakalian et al. The contents of the "other conditions" field in the record 401-5 indicate a seventh condition based on the electron density.

Figure 5:
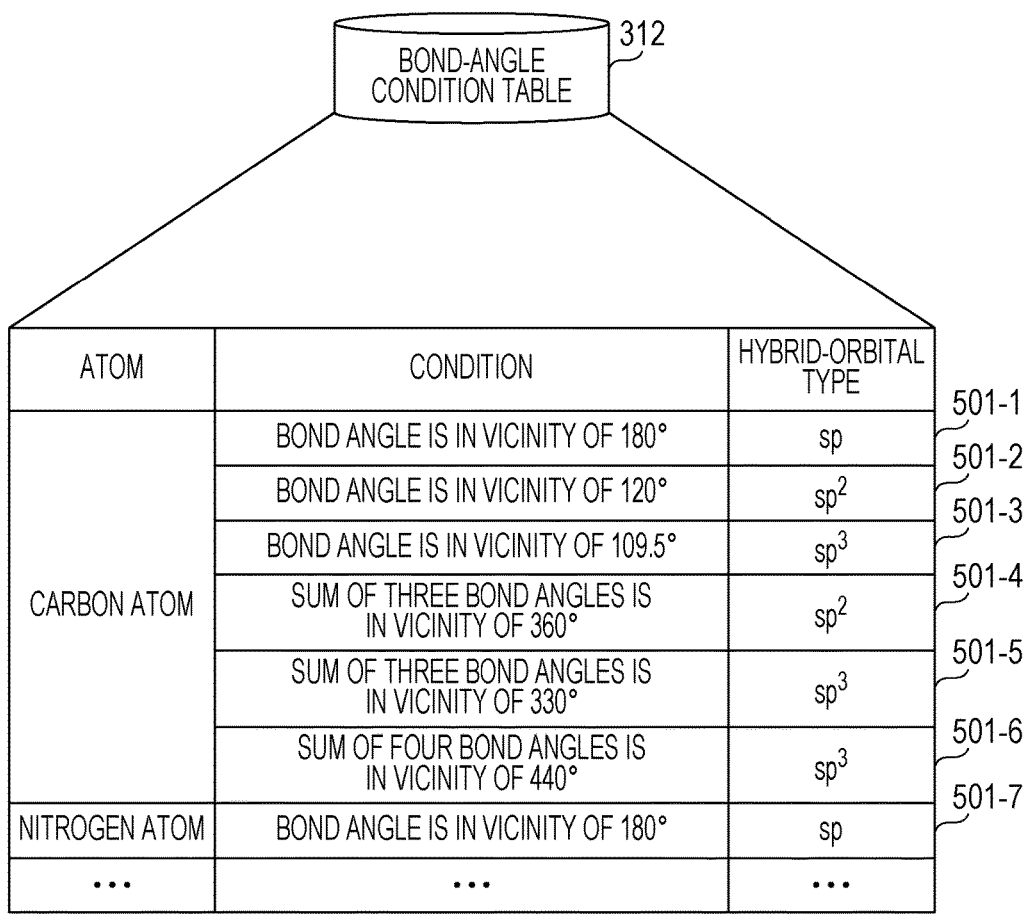
FIG. 5 illustrates an example of the contents stored in a bond-angle condition table.

FIG. 5 illustrates an example of the contents stored in the bond-angle condition table 312. The bond-angle condition table 312 illustrated in FIG. 5 has records 501-1 to 501-7. The bond-angle condition table 312 includes three fields, that is, an "atom" field, a "condition" field, and a "hybrid-orbital type" field. The type of atom is stored in the "atom" field. A condition to be satisfied by a bond angle centered on the corresponding atom is stored in the "condition" field. More specifically, a condition resulting from representation of a bond angle by using a pre-designated threshold is stored in the "condition" field. The hybrid orbital type of the atom at the center of a bond angle when the bond angle satisfies the condition stored in the corresponding "condition" field is stored in the "hybrid-orbital type" field.

The pre-designated threshold may be designated in increments of about 2° to 3° and has a small dependency on the calculation accuracy. In the present embodiment, the pre-designated threshold is in increments of 2.5°. When a method for determining a bond type by using a bond distance is used, the threshold is designated in increments of 0.001 angstrom, and thus the dependency on calculation accuracy increases.

For example, the record 501-1 indicates that, when the bond angle centered on a carbon atom is in the vicinity of 180°, the carbon atom in question is an sp atom. The record 501-4 indicates that, when the sum of three bond angles is in the vicinity of 360°, the carbon atom at the center of the bond angles is an $sp^2$ atom.

Now, a description will be given of the "vicinity of x degrees" indicated in the records 501-1 to 501-7. In this case, x denotes the angle stored in the "condition" field of each record. As a first decision method, the identifying apparatus 101 may decide that the condition is satisfied, for example, when the bond angle or the sum of bond angles is in a predetermined range from x degrees, the predetermined range being designated by the user of the identifying apparatus 101 or the like.

As a second decision method, the identifying apparatus 101 may also decide that the bond-angle condition denoted by the corresponding one of the records 501-1 to 501-3 is satisfied when the bond angle is included in a range determined from an average value of two thresholds. For example, for the condition in the record 501-1, the identifying apparatus 101 may decide that the condition is satisfied when the bond angle is 150° (=(180+120)/2) or more. In addition, for the condition in the record 501-2, the identifying apparatus 101 may decide that the condition is satisfied when the bond angle is less than 150° and is 114.8° (=(120+109.5)/2) or more. For the condition in the record 501-3, the identifying apparatus 101 may decide that the condition is satisfied when the bond angle is less than 114.8°.

Using a similar approach, for each of the bond-angle-sum conditions in the records 501-4 and 501-5, the identifying apparatus 101 may decide that the corresponding condition is satisfied when the bond angle is included in a range determined from an average value of two thresholds. For example, for the condition in the record 501-4, the identifying apparatus 101 may decide that the condition is satisfied when the bond angle is 345° (=(360+330)/2) or more. For the condition in the record 501-5, the identifying apparatus 101 may decide that the condition is satisfied when the bond angle is less than 345°.

As a third decision method, for each of the bond-angle conditions denoted by the record 501-1 and the record 501-2, the identifying apparatus 101 may set a range for the condition, considering that the sp atoms exhibit a significantly high linearity. For example, as the condition for the record 501-1, the identifying apparatus 101 may decide that the condition is satisfied when the bond angle is 170° (=180-2.5×4) or more. For the condition in the record 501-2, the identifying apparatus 101 may decide that the condition is satisfied when the bond angle is less than 170° and the bond angle is 114.8° or more. In this case, for an atom with a coordination number of 2 and in a 5-membered ring, the bond angle is 108° even for $sp^2$; thus, it is preferable that the atomic species of ring compounds having a ring with 5 members or less be excluded during execution of the method for the atomic-species determination based on the bond angles according to the present embodiment. However, $sp^3$ systems with a coordination number 2 and, such as nitrogen anions, are rare systems.

As a fourth decision method, the identifying apparatus 101 may also set a range for a condition for determining whether a nitrogen atom is an $sp^2$ atom or an $sp^3$ atom, considering that, when an aromatic series such as benzene combines with a nitrogen atom, a lone electron pair in the nitrogen atom is more likely to be delocalized with an aromatic ring. For example, for the condition for an $sp^2$ nitrogen atom, when the sum of bond angles centered on a nitrogen atom in question is less than 352.5° (=360-2.5×3), the identifying apparatus 101 may decide that the condition is satisfied and thus the nitrogen atom is an $sp^2$ nitrogen atom. For the condition for an $sp^3$ nitrogen atom, when the sum of bond angles centered on a nitrogen atom in question is 352.5° or more, the identifying apparatus 101 may decide that the condition is satisfied and the nitrogen atom is an $sp^3$ nitrogen atom.

Figure 6:
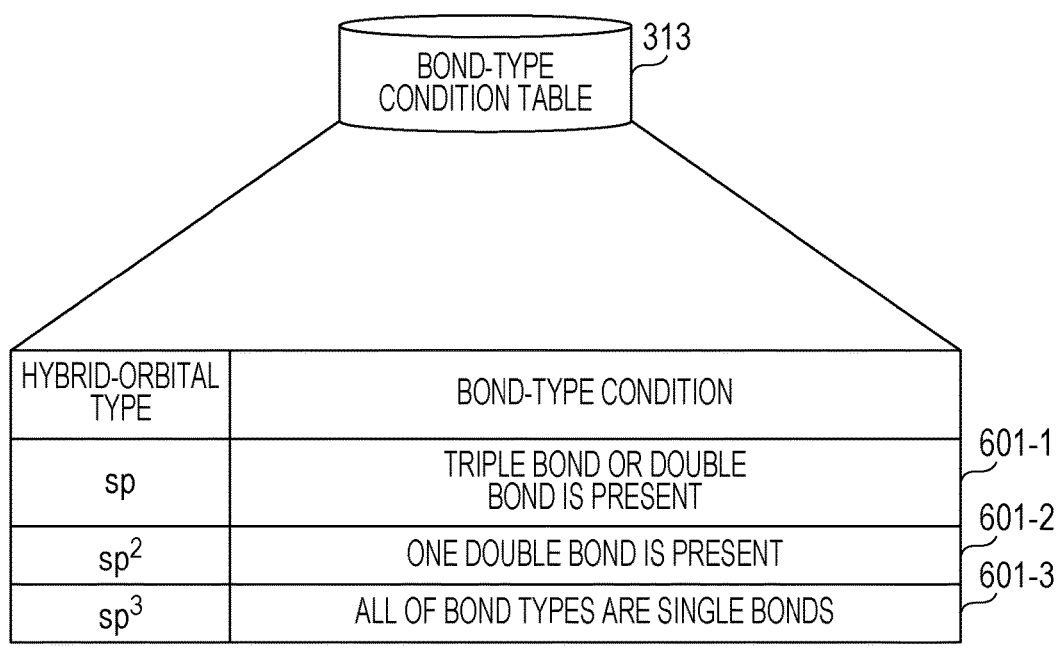
FIG. 6 illustrates an example of bond-type conditions corresponding to the types of hybrid orbital.

FIG. 6 illustrates an example of bond-type conditions corresponding to the types of hybrid orbital. FIG. 6 illustrates the bond-type condition table 313 that stores therein bond-type conditions corresponding to the types of hybrid orbital. The bond-type condition table 313 illustrated in FIG. 6 has records 601-1 to 601-3.

The bond-type condition table 313 includes two fields, that is, a "hybrid-orbital type" field and a "bond-type condition" field. In this case, sp, $sp^2$, and $sp^3$ are stored in the "hybrid-orbital type" fields as the hybrid orbital types of atoms. A condition to be satisfied by the types of bonds between an atom and multiple atoms that combine with the atom, when the hybrid orbital type of the atom is a type stored in the "hybrid-orbital type" field, is stored in each "bond-type condition" field.

For example, the record 601-1 indicates that, when the atom is an sp atom, a condition to be satisfied by the type of bond between the atom and each of the atoms that combine with the atom is that a triple bond or double bond is present.

The record 601-2 indicates that, when the atom in is an $sp^2$ atom, a condition to be satisfied by the type of bond between the atom and each of the atoms that combine with the atom is that one double bond is present.

In addition, the record 601-3 indicates that, when the atom is an spa atom, a condition to be satisfied by the type of bond between the atom and each of multiple atoms that combine with the atom is that all of the bond types are single bonds.

Next, a list of atomic species and bond types that can be taken by a nitrogen atom will be described with reference to FIG. 7.

FIG. 7 illustrates an example of atomic species and bond types of nitrogen atoms. A table 701 illustrates atomic species and bond types of nitrogen atoms. All of the atomic species illustrated in FIG. 7 are AM1BCC atomic species.

Nitrogen atoms have a coordination number of 1 to 4. Nitrogen atoms further have three types of state, that is, a cationic state in which the valence is 4, a neutral state in which the valence is 3, and an anionic state in which the valence is 2. If the coordination number is 1 and the state of a nitrogen atom is neutral, then the atomic species is [25] and the bond type is a triple bond. If the coordination number is 1 and the state of a nitrogen atom is an anion, then the atomic species is [25] and the bond type is a double bond.

If the coordination number is 2 and the state of the nitrogen atom is a cation, then the nitrogen atom is an sp atom, the atomic species is [25], and the bond type is a triple bond. If the coordination number is 2 and the state of the nitrogen atom is neutral, then the nitrogen atom is an $sp^2$ atom, the atomic species is [24], and the bond types are a double bond and a single bond. If the coordination number is 2 and the state of the nitrogen atom is an anion, then the nitrogen atom is an $sp^3$ atom, the atomic species is one of [21], [22], and [23], and the bond types are two single bonds.

If the coordination number is 3 and the state of the nitrogen atom is a cation, then the nitrogen atom is an $sp^2$ atom, the atomic species is [23], and the bond types are a double bond and a single bond. If the coordination number is 3 and the state of the nitrogen atom is neutral, then the nitrogen atom is an $sp^3$ atom, the atomic species is [21], [22], or [23], and the bond types are three single bonds.

If the coordination number is 4 and the state of the nitrogen atom is a cation, then the nitrogen atom is an $sp^3$ atom, the atomic species is [21], and the bond types are a double bond and a single bond. Next, an example of the contents stored in a molecule structure table 801, which is a table in which molecule structures are stored, will be described with reference to FIGS. 8A and 8B.

Figure 8A:
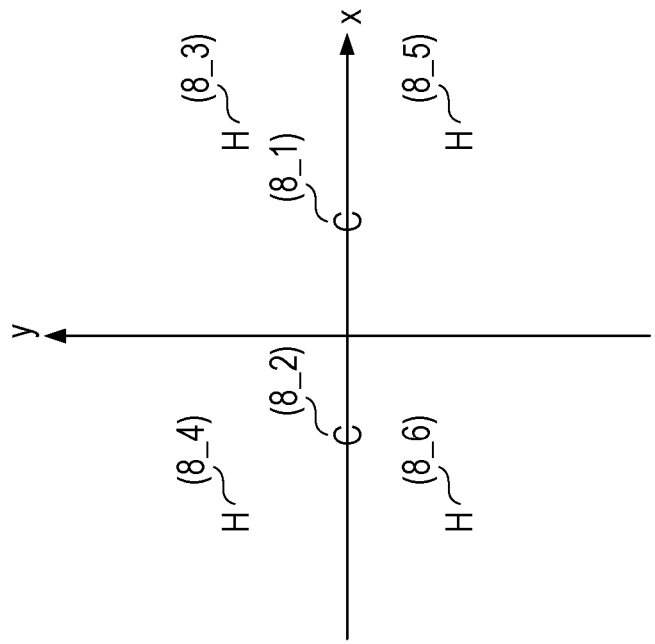
FIGS. 8A and 8B illustrate an example of the contents stored in a molecule structure table.
Figure 8B:
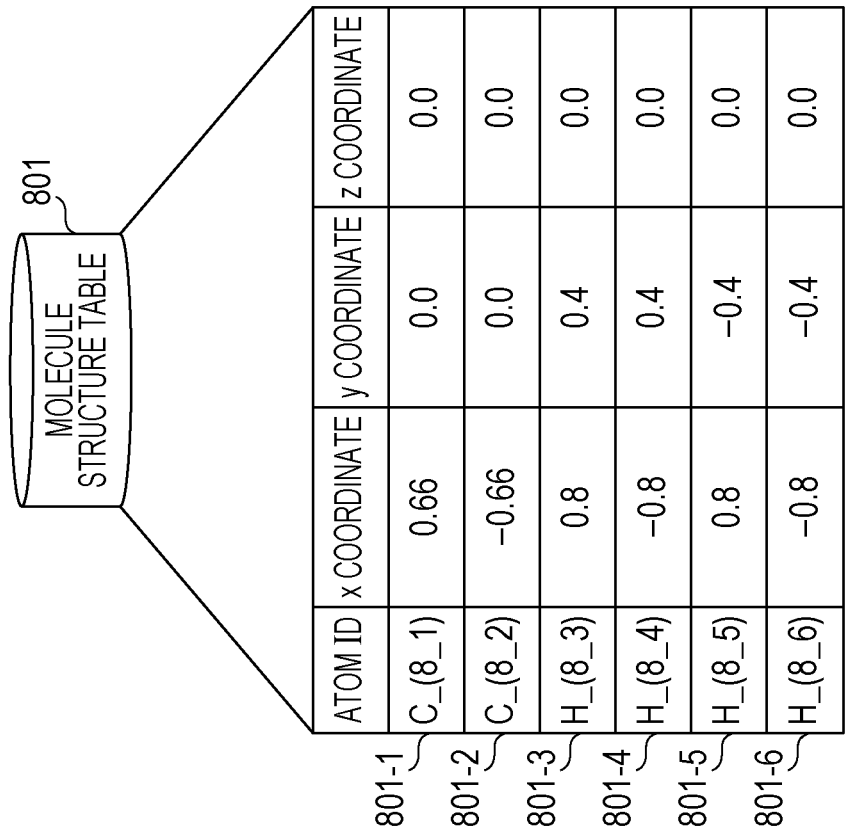

FIGS. 8A and 8B illustrate an example of the contents stored in the molecule structure table 801. A case in which the molecule structures of an ethylene molecule are stored in the molecule structure table 801 will be described by way of example with reference to FIGS. 8A and 8B. FIG. 8A illustrates an example of the contents stored in the molecule structure table 801. FIG. 8B illustrates, on xy coordinates, the positions of atoms corresponding to the contents stored in the molecule structure table 801.

The molecule structure table 801 illustrated in FIG. 8A stores therein records 801-1 to 801-6. The molecule structure table 801 has four fields, that is, an "atom ID" field, an "x coordinate" field, a "y coordinate" field, and a "z coordinate" field. Identification information for identifying a target atom is stored in the "atom ID" field. The value of the x coordinate of the target atom is stored in the "x coordinate" field. The value of the y coordinate of the target atom is stored in the "y coordinate" field. The value of the z coordinate of the target atom is stored in the "z coordinate" field. For example, the record 801-1 indicates that C_(8_1) is located at x coordinate=0.66, y coordinate=0.0, and z coordinate=0.0.

In FIG. 8B, C_(8_1) to H_(8_6) denoted by the records 801-1 to 801-6 are depicted on xy coordinates. Since all of the values of the z coordinates of C_(8_1) to H_(8_6) are 0.0, the z-axis is not depicted in FIG. 8B. Next, processing from generation of the molecule structure of a target molecule $C_{12}H_6O_4$ to assignment of a molecular force field will be described with reference to FIGS. 9A to 13B.

Figure 9A:
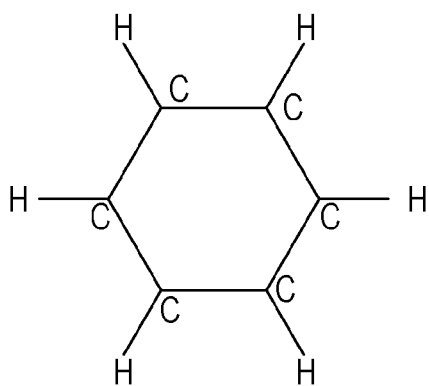
FIGS. 9A to 9C are diagrams illustrating an example of generating an initial value for a molecule structure by using modeling software.
Figure 9B:
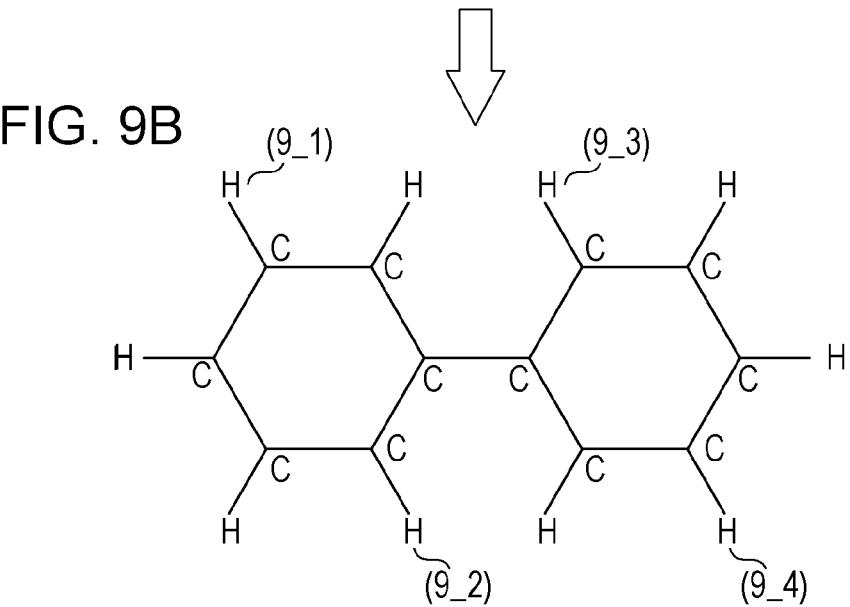
Figure 9C:
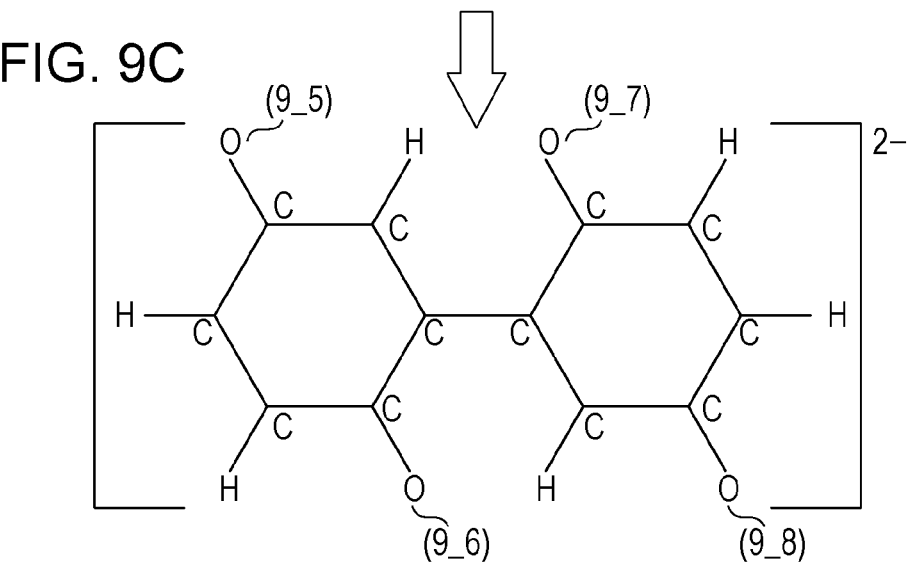

FIGS. 9A to 9C are diagrams illustrating an example of generating an initial value for a molecule structure by using modeling software. A state in which data stored in the molecule structure table 801 is generated by modeling software will now be described with reference to FIGS. 9A, 9B, and 9C.

In FIG. 9A, in accordance with an operation by the user, the identifying apparatus 101 displays a benzene ring. For example, at the identifying apparatus 101, the user operates the mouse 211 to press a benzene ring icon provided on a toolbar. In addition, in accordance with a click operation with the mouse 211 by the user, the identifying apparatus 101 displays a benzene ring at a position in a work window.

Next, in FIG. 9B, in accordance with an operation with the mouse 211 by the user, the identifying apparatus 101 displays a second benzene ring. In addition, in accordance with an operation with the mouse 211 by the user, the identifying apparatus 101 displays a state in which the first benzene ring and the second benzene ring are combined together.

Subsequently, in FIG. 9C, in accordance with an operation with the mouse 211 by the user, the identifying apparatus 101 replaces H_(9_1) to H_(9_4) in FIG. 9B with O_(9_5) to O_(9_8). In addition, in accordance with an operation with the mouse 211 by the user, the identifying apparatus 101 sets the entire charge of the molecule to "−2". Next, the identifying apparatus 101 determines a stable structure for the target molecule $C_{12}H_6O_4$ generated in FIGS. 9A to 9C, by using a molecular orbital method. The calculation with the molecular orbital method is realized by a parametric method 5 (PM5) belonging to the Neglect of Diatomic Differential Overlap (NDDO) method. The identifying apparatus 101 stores, in the position-information table 311, the position information of each of the atoms in the target molecule whose structure has become stable.

Subsequently, using the PM5 method, the identifying apparatus 101 calculates a Mayer bond order of a portion having a bond. The identifying apparatus 101 calculates the Mayer bond order by using expression (1).

$$BO_{kk'} = \sum_{\lambda \in k} \sum_{\omega \in k'} (PS)_{\omega\lambda}(PS)_{\lambda\omega} \qquad (1)$$

In this case, $BO_{kk'}$ denotes the Mayer bond order between an atom k and an atom k'. P denotes a density matrix of electrons, and S denotes an atomic-orbital-overlap integral matrix. Also, λ and ω denote basis functions belonging to k and k', respectively. Since the calculation of the density matrix P and the overlap integral matrix S is performed when the energy is calculated by quantum-mechanical-calculation, and is thus not to be performed as an extra calculation, when the bond order is determined. Accordingly, the amount of calculation for the bond order is negligibly small relative to the quantum-mechanical-calculation. The identifying apparatus 101 calculates matrix components of the density matrix P and matrix components of the overlap integral matrix S, in accordance with equations (2) and (3) below.

$$P_{\mu\nu} = 2 \sum_{i}^{n} C_{\mu i} C_{\nu i} \qquad (2)$$

$$S_{\mu\nu} = \int \chi_\mu \chi_\nu dv \qquad (3)$$

In this case, μ and ν denote suffixes related to the atomic orbitals. $C\mu_i$ and $C\nu_i$ denote the molecular orbitals with the ith lowest one of the potential energies that can be taken by a molecule or orbital coefficients of orbitals in a density functional method. χμ and χν denote basis functions for deploying the molecular orbitals. For example, when there are ten electrons, n is 5. When the ith orbit is represented by $Ψ_i$, the relationship between $Ψ_i$ and $Cμ_i$ and χμ is represented by equation (4).

$$\psi_i = \sum_\mu C_{\mu i} \chi_\mu \quad (4)$$

FIGS. 10A, 10B1, and 10B2 are diagrams illustrating examples of a method for atomic-species determination based on electron densities. FIG. 10A illustrates a method for bond-type determination using electron densities. FIGS. 10B1 and 10B2 illustrate a method for bond-type determination using valences.

In the method in FIG. 10A using electron densities, the identifying apparatus 101 calculates the value of an electron density ρ between O_(10_1) and C_(10_2) to be 1.38. Subsequently, since the value of ρ satisfies the condition "electron density ρ<1.5" indicating a single bond, the identifying apparatus 101 determines that the type of bond between O_(10_1) and C_(10_2) is a single bond. Since the bond type is a single bond, the identifying apparatus 101 determines that the atom in question is anionic oxygen whose valence is 1. Information indicating that the oxygen atom is anionic when the valence of the oxygen atom is 1 and the oxygen atom is neutral when the valence of the oxygen atom is 2 is stored in the RAM 203, the magnetic disk 205, or the optical disk 207 as a table.

The identifying apparatus 101 determines that the value of the electron density ρ between C_(10_4) and O_(10_3) is 1.62. Since ρ satisfies the condition "1.5≤ρ<2.5" indicating a double bond, the identifying apparatus 101 determines that the type of bond between O_(10_3) and C_(10_4) is a double bond. Thus, the identifying apparatus 101 determines that the type of bond is a single bond, when ρ<1.5 is satisfied, and determines that the type of bond is a double bond, when 1.5≤ρ<2.5 is satisfied. Although not illustrated in FIGS. 10A, 10B1, and 10B2, the identifying apparatus 101 determines that the type of bond is a triple bond when 2.5≤ρ is satisfied.

Since the valence of O⁻ is 1 and the valence of O is 2, there are two kinds of structure, that is, the structure depicted in FIG. 10B1 and the structure depicted in FIG. 10B2. Hence, with the atomic-valence-based method illustrated in FIG. 10B, it is difficult to decide the correct one of the structures. Thus, the use of the method using valences leaves ambiguity in its determination. As a structure that can be taken in practice, the structures depicted in FIGS. 10A and 10B1, the structures having anionic oxygen at the diagonal positions, are stable. Accordingly, the use of the method for the determination using electron densities allows the identifying apparatus 101 to more correctly determine a bond type than the method using valences.

FIGS. 11A1, 11A2, 11B1, and 11B2 are diagrams illustrating examples of a method for aromatic-bond determination based on electron densities. A method for determining the type of bond between atoms included in a specific ring structure will now be described with reference to FIGS. 11A1 and 11A2 and FIGS. 11B1 and 11B2. Specifically, in FIGS. 11A1 and 11A2, the identifying apparatus 101 determines the type of bond between atoms included in $C_{12}H_6O_4$. In FIGS. 11B1 and 11B2, the identifying apparatus 101 determine the type of bond between atoms included in $C_6H_6$.

It is assumed that, in FIG. 11A1, the identifying apparatus 101 has determined that the type of bond between H_(11_1) and C_(11_2) is a single bond. Next, the identifying apparatus 101 decides whether or not any of H_(11_1) and C_(11_2) is included in a ring. In the case in FIG. 11A1, since C_(11_2) to C_(11_7) forms a ring, C_(11_2) is included in the ring. The ring formed by C_(11_2) to C_(11_7) is hereinafter referred to as a "ring 1101". Since C_(11_2) is included in the ring 1101, the identifying apparatus 101 decides whether or not a combination of the group of atoms forming the ring 1101 is a specific combination. The term "specific combination" as used herein corresponds to the atomic condition in the record 401-5 illustrated in FIG. 4. In this case, since all of the atoms in the atom group forming the ring 1101 are carbon atoms, this atom group is the specific combination.

When the ring 1101 is the specific combination, the identifying apparatus 101 decides whether the type of bond between the ring 1101 and an atom that combines with the ring 1101 is a single bond or a coordination bond. In the stage illustrated in FIG. 11A1, since the type of bond between the ring 1101 and an atom that combines with the ring 1101, for example, the type of bond between C_(11_7) and O⁻_(11_8), has not been determined yet, the identifying apparatus 101 does not decide whether or not the type of bond between the atoms in the ring 1101 is an aromatic bond.

Next, it is assumed that, in FIG. 11A2, the identifying apparatus 101 has determined the type of bond between C_(11_7) and O⁻_(11_8) is a single bond. It is also assumed that the identifying apparatus 101 has determined all of the types of bonds between the ring 1101 and the atoms that combine with the ring 1101. Since C_(11_7) is included in the ring 1101, the identifying apparatus 101 then decides whether the type of bond between the ring 1101 and an atom that combines with the ring 1101 is a single bond or a coordination bond. Since some of the types of bonds that contact the ring 1101, such as the double bond between C_(11_3) and C_(11_9), are neither a single bond nor a coordination bond, the identifying apparatus 101 decides that the types of the bonds between the atoms in the ring 1101 are not aromatic bonds. The types of the bonds between the atoms in the ring 1101 are determined by the method using electron densities, the method being described with reference to FIGS. 10A, 10B1, and 10B2.

It is also assumed that, in FIG. 11B1, the identifying apparatus 101 has determined that the type of bond between H_(11_11) and C_(11_12) is a single bond. Next, the identifying apparatus 101 decides whether or not any of H_(11_11) and C_(11_12) is included in a ring. In the case illustrated in FIG. 11B1, since C_(11_12) to C_(11_17) form a ring, C_(11_12) is included in the ring. The ring formed by C_(11_12) to C_(11_17) is hereinafter referred to as a "ring 1102". In the state illustrated in FIG. 11B1, since some of the types of bonds between the ring 1102 and atoms that combine with the ring 1102 have not been determined yet, the identifying apparatus 101 does not decide whether or not the type of bond between atoms included in the ring 1102 is an aromatic bond.

Next, it is assumed that, in FIG. 11B2, the identifying apparatus 101 has determined that the type of bond between C_(11_17) and H_(11_18) is a single bond. Since C_(11_17) is included in the ring 1102, the identifying apparatus 101 decides whether the type of bond between the ring 1102 and an atom that combines with the ring 1102 is a single bond or a coordination bond. Since all of the types of bonds between the ring 1102 and the atoms that combine with the ring 1102 are single bonds, the identifying apparatus 101 decides that the types of bonds between the atoms included in the ring 1102 are aromatic bonds.

Figure 12A:
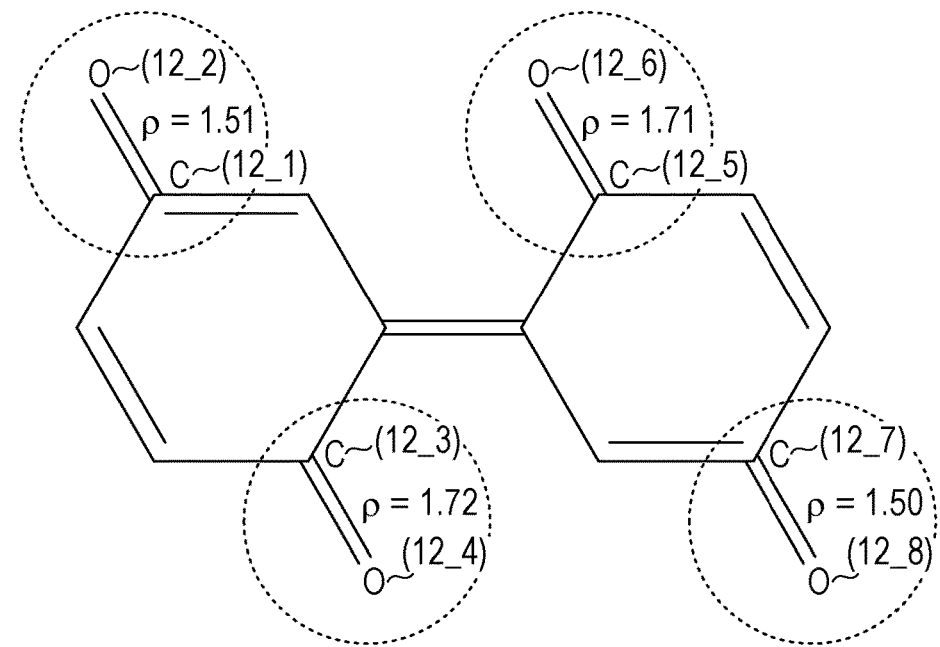
FIGS. 12A and 12B are diagrams illustrating an example of a method for determining a type of bond with a charge by using electron densities.
Figure 12B:
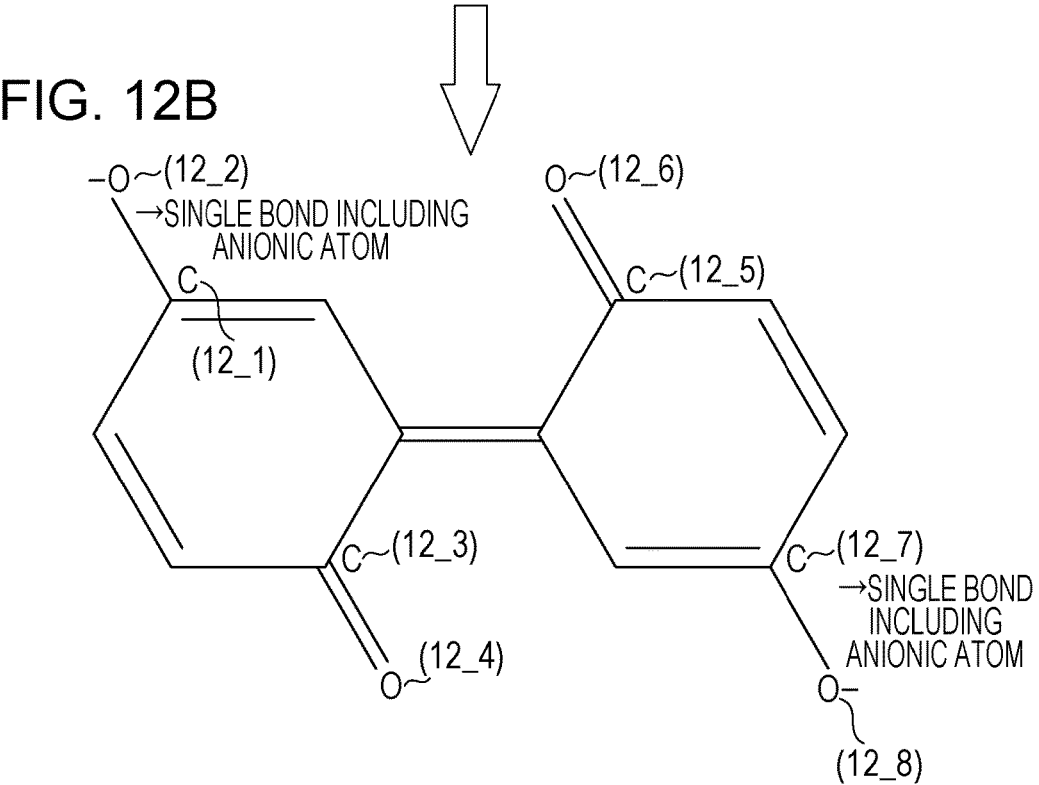

FIGS. 12A and 12B are diagrams illustrating an example of a method for determining a type of bond with a charge by using electron densities. The value of the electron density of a single bond including an anionic atom is larger than that of a single bond between neutral atoms, and may exceed a threshold "1.5" for deciding whether the type of bond is a single bond or a double bond. A method for determining a single bond including an anionic atom when the value of the electron density exceeds the threshold "1.5" will now be described with reference to FIGS. 12A and 12B.

The identifying apparatus 101 extracts, of combinations of atoms in a target molecule $C_{12}H_6O_4$, pairs in which the type of bond is a double bond. In FIG. 12A, the identifying apparatus 101 extracts a pair of C_(12_1) and O_(12_2), a pair of C_(12_3) and O_(12_4), a pair of C_(12_5) and O_(12_6), and a pair of C_(12_7) and O_(12_8). It is also assumed that the value of the electron density ρ between C_(12_1) and O_(12_2) is 1.51 and the value of the electron density ρ between C_(12_3) and O_(12_4) is 1.72. It is further assumed that the value of the electron density ρ between C_(12_5) and O_(12_6) is 1.71 and the value of the electron density ρ between C_(12_7) and O_(12_8) is 1.50.

Since all of the extracted four pairs are combinations of carbon atoms and oxygen atoms, the identifying apparatus 101 continues the processing on the four pairs. If the combination of two atoms in the extracted pair is different from the combination in another extracted pair, the identifying apparatus 101 classifies the extracted combinations into groups according to the types of two atoms and continues the processing for each group. For example, when the extracted combinations are constituted of a combination of a carbon atom and a carbon atom and a combination of a carbon atom and an oxygen atom, the identifying apparatus 101 sets the combination of the carbon atom and the carbon atom as one group and sets the combination of the carbon atom and the oxygen atom as another group.

Next, the identifying apparatus 101 decides whether or not the values of the electron densities of the four extracted pairs are the same. For example, not only when the values of the electron densities of the pairs are exactly the same, but also when the difference between the values of the electron densities to be compared is smaller than or equal to a predetermined threshold, it may be regarded in the decision that the values of the electron densities are the same. In the example in FIG. 12A, it is assumed that, when the difference between the values of the electron densities to be compared is less than 0.05, it is regarded that the values are the same. For example, since the value of the electron density between C_(12_1) and O_(12_2) is 1.51 and the value of the electron density between C_(12_3) and O_(12_4) is 1.72, 1.72−1.51=0.21>0.05 is given, and thus, the identifying apparatus 101 decides that the values are not the same. Similarly, the identifying apparatus 101 decides that the value of the electron density between C_(12_5) and O_(12_6) and the value of the electron density between C_(12_7) and O_(12_8) are not the same.

Upon deciding that the values of the electron densities are not the same, the identifying apparatus 101 determines that the type of bond having a smaller one of the values of the electron densities is a single bond. FIG. 12B illustrates a state after the determination. The identifying apparatus 101 determines that the type of bond between C_(12_1) and O_(12_2) is a single bond and further sets O_(12_2) to O⁻_(12_2). Similarly, the identifying apparatus 101 determines that the type of bond between C_(12_7) and O_(12_8) is a single bond and further sets O_(12_8) to O⁻_(12_8). Next, an example of atomic-species determination using the determined bond types illustrated in FIGS. 10A to 12B will be described with reference to FIGS. 13A and 13B.

Figure 13A:
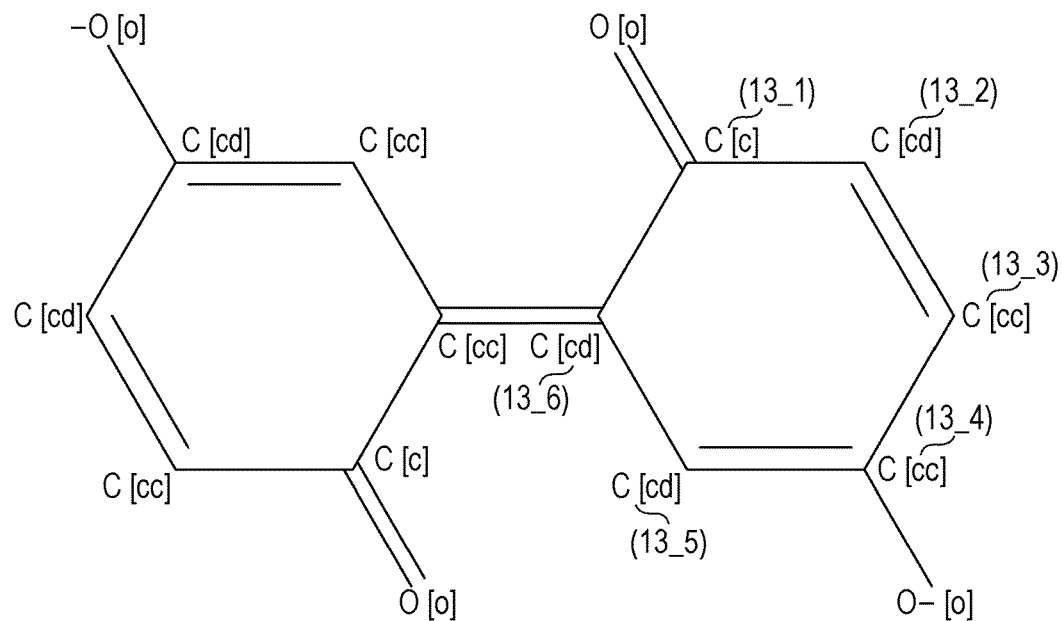
FIGS. 13A and 13B are diagrams illustrating an example of a result of the atomic-species determination based on electron densities.
Figure 13B:
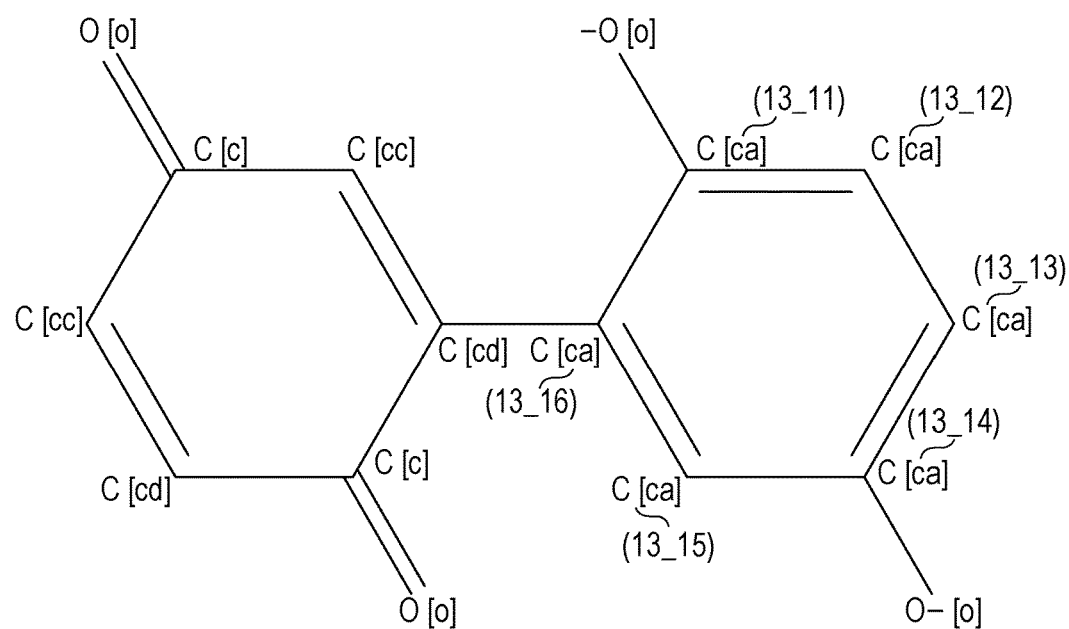

FIGS. 13A and 13B are diagrams illustrating examples of a result of the atomic-species determination based on electron densities. With respect to a target molecule $C_{12}H_6O_4$, FIG. 13A illustrates atomic species in the structure illustrated in FIG. 10A, and FIG. 13B illustrates atomic species in the structure illustrated in FIG. 10B2.

The atomic species can be identified on a one-to-one basis by using the bond types. FIGS. 13A and 13B illustrate a case in which GAFF atomic species are used. Although hydrogen atoms are not illustrated in FIGS. 13A and 13B, the GAFF atomic species of all of the hydrogen atoms are [ha].

In FIG. 13A, the identifying apparatus 101 determines that the GAFF atomic species of C_(13_1), C_(13_2), C_(13_3), C_(13_4), C_(13_5), and C_(13_6) are [c], [cd], [cc], [cc], [cd], and [cd], respectively.

In FIG. 13B, the identifying apparatus 101 also determines that all of the GAFF atomic species of C_(13_11) to C_(13_16) are [ca]. When the GAFF atomic species vary, a molecular force field to be assigned also varies, which affects simulation involving parameters and so on.

As illustrated in FIGS. 13A and 13B, when the atomic species vary, a force field to be assigned also varies, the result of the simulation becomes inaccurate. The identifying apparatus 101 according to the present embodiment can also assign an appropriate molecular force field to a new molecule.

The method for the atomic-species determination based on electron densities has been described above with reference to FIGS. 10A to 13B. Next, an example of a method for atomic-species determination based on bond angles will be described with reference to FIGS. 14A and 14B.

Figure 14B:
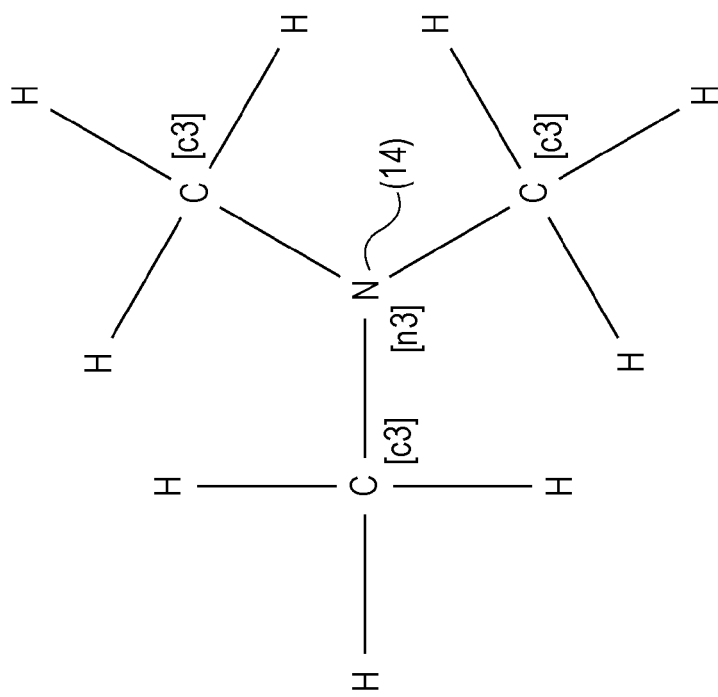
FIGS. 14A and 14B are diagrams illustrating an example of a method for atomic-species determination based on bond angles.
Figure 14A:
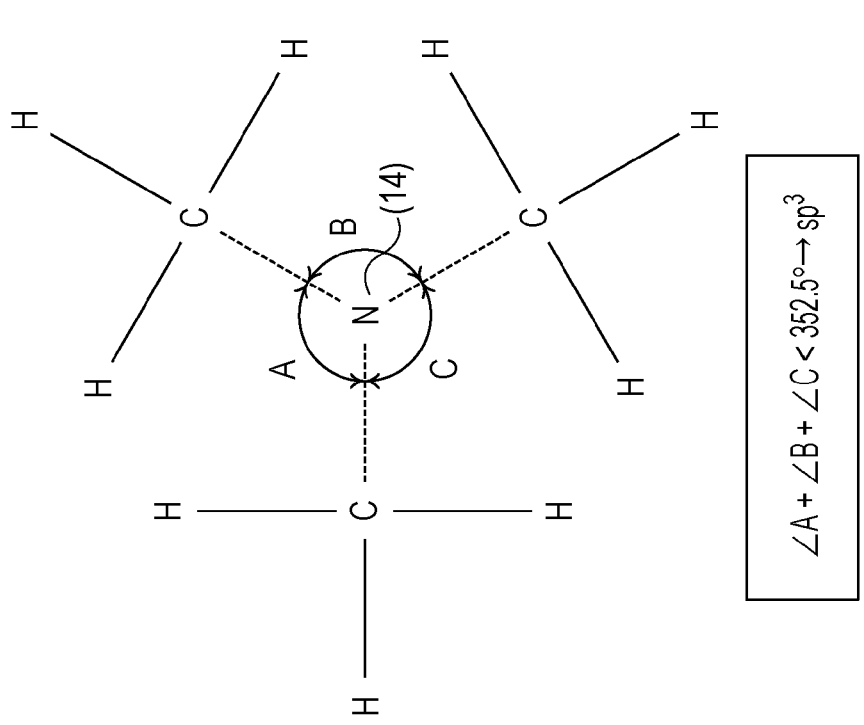

FIGS. 14A and 14B are diagrams illustrating an example of the method for the atomic-species determination based on bond angles. A method for atomic-species determination based on bond angles when the target molecule is $C_3H_9N$ will be described with reference to FIGS. 14A and 14B.

In FIG. 14A, the identifying apparatus 101 searches for a structurally stable state of the target molecule. After successfully detecting a structurally stable state, the identifying apparatus 101 calculates three bond angles centered on N_(14), that is, ∠A, ∠B, and ∠C in FIG. 14A, when the target molecule is in the detected structurally stable state. The result of the calculation indicates that all of ∠A, ∠B, and ∠C in FIG. 14A are 113°, and ∠A+∠B+∠C in FIG. 14A=339°<352.5° is given. Thus, the identifying apparatus 101 decides that N_(14) is an $sp^3$ nitrogen atom.

Subsequently, in FIG. 14B, since N_(14) combines with methyl groups having carbon atoms whose GAFF atomic species is [c3], the identifying apparatus 101 determines that the GAFF atomic species of N_(14) is [n3]. Next, an example of a result of the atomic-species determination based on bond angles will be described with reference to FIGS. 15A to 17C.

FIGS. 15A to 15D are diagrams (part 1) illustrating examples of a result of the atomic-species determination based on bond angles. FIGS. 15A to 15D illustrate how the atomic species of an atom located at the center of bond angles are determined based on the bond angles with respect to respective six target molecules. A case in which the atom located at the center of the bond angles is a carbon atom will be described with reference to FIGS. 15A to 15D.

Figure 15A:
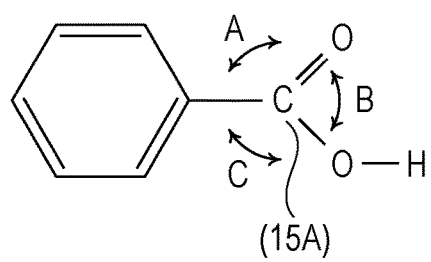
FIGS. 15A to 15D are diagrams (part 1) illustrating examples of a result of the atomic-species determination based on bond angles.

In FIG. 15A, the identifying apparatus 101 determines the atomic species of C_(15A) in a target molecule $C_7H_6O_2$ by using bond angles centered on C_(15A). The identifying apparatus 101 searches for a structurally stable state of the target molecule. After successfully detecting a structurally stable state, the identifying apparatus 101 calculates three bond angles centered on C_(15A), that is, ∠A, ∠B, and ∠C in FIG. 15A, when the target molecule is in the detected structurally stable state. The result of the calculation indicates that ∠A, ∠B, and ∠C in FIG. 15A are 115.4°, 116.0°, and 128.6°, respectively, and ∠A+∠B+∠C=360.0°≥352.5° is given. Thus, the identifying apparatus 101 decides that C_(15A) is an sp$^2$ carbon atom.

Subsequently, since C_(15A) combines with oxygen atoms, the identifying apparatus 101 can decide that the C_(15A) is a carbonyl carbon. Thus, the identifying apparatus 101 determines that the GAFF atomic species of C_(15A) is [c].

Figure 15B:
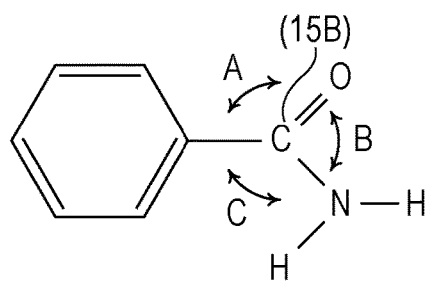

In FIG. 15B, the identifying apparatus 101 determines the atomic species of C_(15B) in a target molecule $C_7H_7ON$ by using bond angles centered on C_(15B). The identifying apparatus 101 searches for a structurally stable state of the target molecule. After successfully detecting a structurally stable state, the identifying apparatus 101 calculates three bond angles centered on C_(15B), that is, ∠A, ∠B, and ∠C in FIG. 15B, when the target molecule is in the detected structurally stable state. The result of the calculation indicates that ∠A, ∠B, and ∠C in FIG. 15B are 121.9°, 119.7°, and 118.3°, respectively, and ∠A+∠B+∠C=359.9°≥352.5° is given. Thus, the identifying apparatus 101 decides that C_(15B) is an sp$^2$ carbon atom.

Subsequently, since C_(15B) combines with an oxygen atom and a nitrogen atom, the identifying apparatus 101 may also decide that C_(15B) is an amide carbon. Thus, the identifying apparatus 101 determines that the GAFF atomic species of C_(15B) is [c].

Figure 15C:
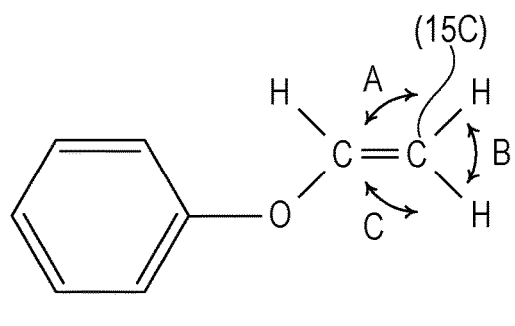

In FIG. 15C, the identifying apparatus 101 determines the atomic species of C_(15C) in a target molecule $C_8H_8O$ by using bond angles centered on C_(15C). The identifying apparatus 101 searches for a structurally stable state of the target molecule. After successfully detecting a structurally stable state, the identifying apparatus 101 calculates three bond angles centered on C_(15C), that is, ∠A, ∠B, and ∠C in FIG. 15C, when the target molecule is in the detected structurally stable state. The result of the calculation indicates that ∠A, ∠B, and ∠C in FIG. 15C are 120.9°, 116.4°, and 122.7°, respectively, and ∠A+∠B+∠C=360.0°≥352.5° is given. Thus, the identifying apparatus 101 decides that C_(15C) is an sp$^2$ carbon atom.

Subsequently, since C_(15C) combines with a carbon atom and hydrogen atoms, the identifying apparatus 101 determines that the GAFF atomic species of C_(15C) is [c2].

Figure 15D:
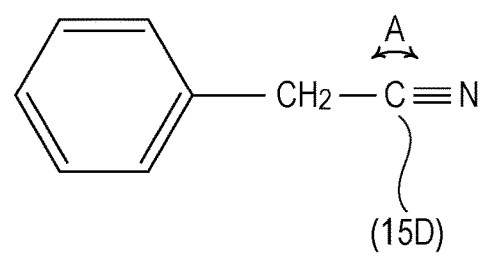

In FIG. 15D, the identifying apparatus 101 determines the atomic species of C_(15D) in a target molecule $C_8H_7N$ by using bond angles centered on C_(15D). The identifying apparatus 101 searches for a structurally stable state of the target molecule. After successfully detecting a structurally stable state, the identifying apparatus 101 calculates an angle centered on C_(15D), that is, ∠A in FIG. 15D, when the target molecule is in the detected structurally stable state. The result of the calculation indicates that ∠A in FIG. 15D is 178.3°, and ∠A=178.3°≥170.0° is given. Thus, the identifying apparatus 101 decides that C_(15D) is an sp carbon atom. Subsequently, the identifying apparatus 101 determines that the GAFF atomic species of C_(15D) is [c1].

FIGS. 16A to 16F are diagrams (part 2) illustrating examples of a result of the atomic-species determination based on bond angles. FIGS. 16A to 16F illustrate how the atomic species of an atom located at the center of bond angles are determined based on bond angles with respect to respective six target molecules. A case in which the atom located at the center of the bond angles is a nitrogen atom will be described with reference to FIGS. 16A to 16F.

Figure 16A:
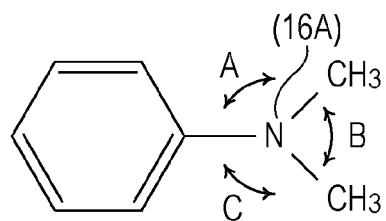
FIGS. 16A to 16F are diagrams (part 2) illustrating examples of a result of the atomic-species determination based on bond angles.

In FIG. 16A, the identifying apparatus 101 determines the atomic species of N_(16A) in a target molecule $C_8H_{11}N$ by using bond angles centered on N_(16A). The identifying apparatus 101 searches for a structurally stable state of the target molecule. After successfully detecting a structurally stable state, the identifying apparatus 101 calculates three bond angles centered on N_(16A), that is, ∠A, ∠B, and ∠C in FIG. 16A, when the target molecule is in the detected structurally stable state. The result of the calculation indicates that ∠A, ∠B, and ∠C in FIG. 16A are 115.6°, 113.4°, and 116.4°, respectively, and ∠A+∠B+∠C=345.4°<352.5° is given. Thus, the identifying apparatus 101 decides that N_(16A) is an sp$^3$ nitrogen atom.

Subsequently, since N_(16A) combines with an aromatic ring, the identifying apparatus 101 determines that the GAFF atomic species of N_(16A) is [nh].

Figure 16B:
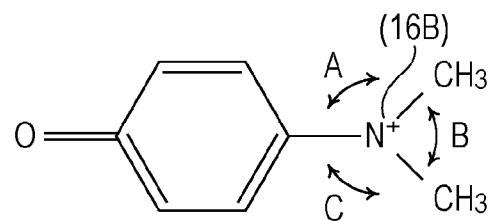

In FIG. 16B, the identifying apparatus 101 determines the atomic species of N_(16B) in a target molecule $C_8H_{10}NO$ by using bond angles centered on N_(16B). In addition, it is assumed that the charge of the target molecule in FIG. 16B is +1. The identifying apparatus 101 searches for a structurally stable state of the target molecule. After successfully detecting a structurally stable state, the identifying apparatus 101 calculates three bond angles centered on N_(16B), that is, ∠A, ∠B, and ∠C in FIG. 16B, when the target molecule is in the detected structurally stable state. The result of the calculation indicates that ∠A, ∠B, and ∠C in FIG. 16B are 121.3°, 117.4°, and 121.3°, respectively, and, ∠A+∠B+∠C=360.0°≥352.5° is given. Thus, the identifying apparatus 101 decides that N_(16B) is an sp$^2$ nitrogen atom.

Subsequently, since the coordination number of N_(16B) is 3, the identifying apparatus 101 decides that N_(16B) is an iminium ion. The identifying apparatus 101 also determines that the AM1BCC atomic species of N_(16B) is [23]. The GAFF atomic species when the target atom is an iminium ion is undefined.

Figure 16C:
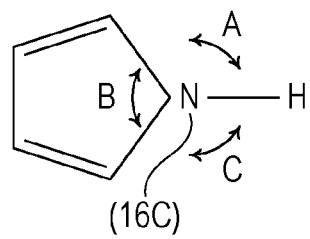

In FIG. 16C, the identifying apparatus 101 determines the atomic species of N_(16C) in a target molecule $C_4H_5N$ by using bond angles centered on N_(16C). The identifying apparatus 101 searches for a structurally stable state of the target molecule. After successfully detecting a structurally stable state, the identifying apparatus 101 calculates three bond angles centered on N_(16C), that is, ∠A, ∠B, and ∠C in FIG. 16C, when the target molecule is in the detected structurally stable state. The result of the calculation indicates that ∠A, ∠B, and ∠C in FIG. 16C are 125.6°, 125.6°, and 108.8°, respectively, and ∠A+∠B+∠C=360.0°≥352.5° is given. Thus, the identifying apparatus 101 decides that N_(16C) is an sp$^2$ nitrogen atom.

Subsequently, since N_(16C) has a coordination number of 3 and is in an aromatic series 5-membered ring, the identifying apparatus 101 decides that N_(16C) is an aromatic sp$^2$ nitrogen atom and the GAFF atomic species is [na].

Figure 16D:
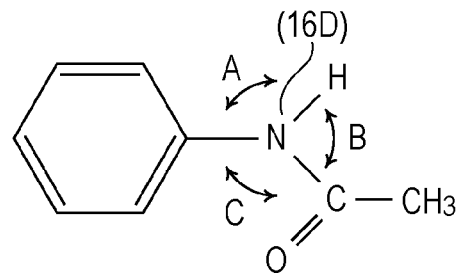

In FIG. 16D, the identifying apparatus 101 determines the atomic species of N_(16D) in a target molecule $C_7H_9NO$ by using bond angles centered on N_(16D). The identifying apparatus 101 searches for a structurally stable state of the target molecule. After successfully detecting a structurally stable state, the identifying apparatus 101 calculates three bond angles centered on N_(16D), that is, ∠A, ∠B, and ∠C in FIG. 16D, when the target molecule is in the detected structurally stable state. The result of the calculation indicates that ∠A, ∠B, and ∠C in FIG. 16D are 115.3°, 116.8°, and 127.9°, respectively, and ∠A+∠B+∠C=360.0°≥352.5° is given. Thus, the identifying apparatus 101 decides that N_(16D) is an sp$^2$ nitrogen atom.

Subsequently, since N_(16D) has a coordination number of 3 and combines with a carbonyl carbon, the identifying apparatus 101 decides that N_(16D) is an amide $sp^2$ nitrogen atom and the GAFF atomic species is [n].

Figure 16E:
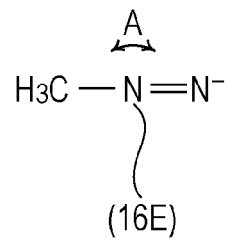

In FIG. 16E, the identifying apparatus 101 determines the atomic species of N_(16E) in a target molecule $CH_3N_2$ by using bond angles centered on N_(16E). The identifying apparatus 101 searches for a structurally stable state of the target molecule. After successfully detecting a structurally stable state, the identifying apparatus 101 calculates an angle centered on N_(16E), that is, ∠A in FIG. 16E, when the target molecule is in the detected structurally stable state. The result of the calculation indicates that ∠A in FIG. 16E is 122.1°, and 114.8°≤∠A=122.1°<170.0° is given. Thus, the identifying apparatus 101 decides that N_(16E) is an $sp^2$ nitrogen atom.

Subsequently, the identifying apparatus 101 decides that the GAFF atomic species of N_(16E) is [n2]. The identifying apparatus 101 also decides that AM1BCC atomic species of N_(16E) is [24].

Figure 16F:
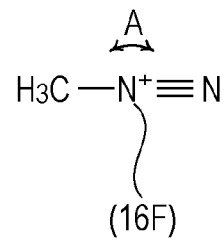

In FIG. 16F, the identifying apparatus 101 determines the atomic species of N_(16F) in a target molecule $CH_3N_2$ by using bond angles centered on N_(16F). The identifying apparatus 101 searches for a structurally stable state of the target molecule. After successfully detecting a structurally stable state, the identifying apparatus 101 calculates an angle centered on N_(16F), that is, ∠A in FIG. 16F, when the target molecule is in the detected structurally stable state. The result of the calculation indicates that ∠A in FIG. 16F is 180.0°, and ∠A=180.0°≥170.0° is given. Thus, the identifying apparatus 101 decides that N_(16F) is an sp nitrogen atom.

Subsequently, the identifying apparatus 101 decides that the GAFF atomic species of N_(16F) is [n1]. The identifying apparatus 101 also decides that the AM1BCC atomic species of N_(16F) is [25].

Figure 17A:
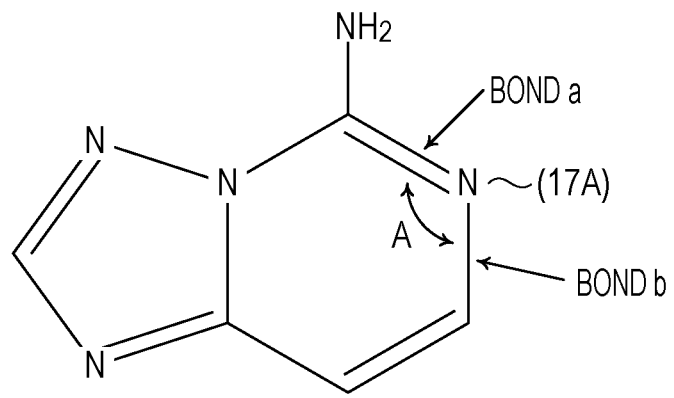
FIGS. 17A to 17C are diagrams (part 3) illustrating examples of a result of the atomic-species determination based on bond angles.
Figure 17B:
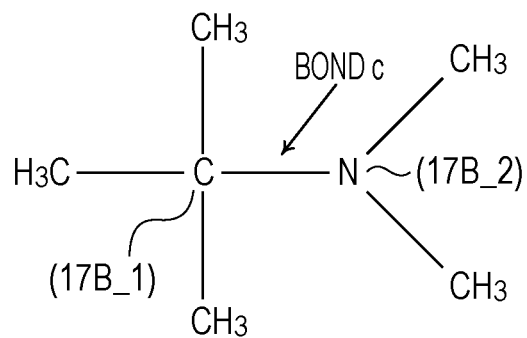
Figure 17C:
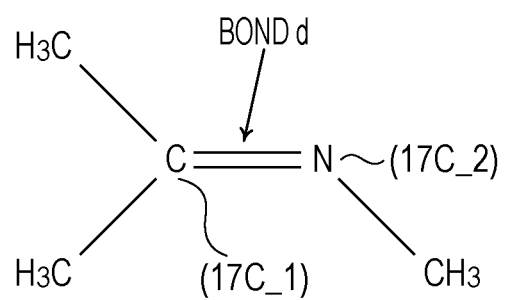

FIGS. 17A to 17C are diagrams (part 3) illustrating examples of a result of the atomic-species determination based on bond angles. Examples in which, when a contradiction occurs in bond types determined using the bond distances or electron densities, the bond types are determined using hybrid atomic orbital types based on bond angles will be described with reference to FIGS. 17A to 17C. In FIG. 17A, for a target molecule $C_5H_5N_4$, the bond type of a bond a and the bond type of a bond b are determined. In this case, the identifying apparatus 101 or another apparatus that is different from the identifying apparatus 101 may determine the bond type of the bond a and the bond type of the bond b. When the other apparatus determines the bond type of the bond a and the bond type of the bond b, the identifying apparatus 101 obtains a result of the determination from the other apparatus. A case in which the identifying apparatus 101 determines the bond type of the bond a and the bond type of the bond b will be described with reference to FIGS. 17A to 17C.

An example of bond-type determination using bond distances will now be described as a first bond-type determination method. The identifying apparatus 101 calculates the distance of the bond a to be 1.357 angstrom and calculates the distance of the bond b to be 1.367 angstrom.

In addition, in order to determine a threshold for deciding the type of bond between a carbon and a nitrogen, the identifying apparatus 101 calculates the distance of a bond c between C_(17B_1) and N_(17B_2) illustrated in FIG. 17B and the distance of a bond d between C_(17C_1) and N_(17C_2) illustrated in FIG. 17C. The identifying apparatus 101 calculates the distance of the bond c to be 1.480 [angstrom] and also calculates the distance of the bond d to be 1.294 [angstrom]. The identifying apparatus 101 then sets a value, used as the threshold for deciding whether the type of bond between a carbon and a nitrogen is a single bond or a double bond, to the average value (1.480+1.294)/2=1.387 of the bond c and the bond d.

Subsequently, the identifying apparatus 101 compares each of the distances of the bonds a and b with the set threshold to decide whether the type of bond is a single bond or a double bond. Since both of the bonds a and b are smaller than the set threshold, the identifying apparatus 101 decides that both of the bonds a and b are double bonds. In this case, this result contradicts the information in the table 701, since the coordination number is 2 and the types of bonds of the neutral nitrogen atoms are a double bond and a single bond, as illustrated in the table 701.

Next, a description will be given of an example of a bond-type determination using electron densities will be described as a second bond-type determination method. The identifying apparatus 101 calculates the electron density of the bond a to be 1.449 and also determines the electron density of the bond b to be 1.264.

Since the records 401-1 and 401-2 indicate that the threshold for deciding whether or not a bond in question is a single bond or a double bond is 1.5, the identifying apparatus 101 determines that both of the bonds a and b are single bonds. In this case, this result contradicts the information in the table 701, since the coordination number is 2 and the types of bonds of the neutral nitrogen atoms are a double bond and a single bond, as illustrated in the table 701.

Accordingly, with respect to the example illustrated in FIG. 17A, the identifying apparatus 101 uses the hybrid orbital type identified using the bond angles and determines the bond type by deciding whether or not the condition for the bond type corresponding to the hybrid orbital type.

More specifically, the identifying apparatus 101 calculates a bond angle centered on N_(17A), that is, ∠A in FIG. 17A. The result of the calculation indicates that ∠A in FIG. 17A is 119.1°, and 114.8°≤∠A=119.1°<170.0° is given. Thus, the identifying apparatus 101 decides that N_(17A) is an $sp^2$ nitrogen atom. When the bond-type condition table 313 is referred to, the $sp^2$ atom has one double bond and has a coordination number of 2. Thus, the identifying apparatus 101 identifies that the types of bonds of N_(17A) are one double bond and one single bond.

Next, the identifying apparatus 101 uses the bond distances or the electron densities to determine which of the bonds a and b is a double bond and which is a single bond. When the bond distances are used, the bond distance of the bond b is larger than that of the bond a. Thus, the identifying apparatus 101 decides that the bond b is closer to a single bond than the bond a, and updates the bond type of the bond b having the larger distance from the double bond to the single bond. When the electron density is used, the electron density of the bond a is higher than that of the bond b. Thus, the identifying apparatus 101 decides that the bond a is closer to a double bond than the bond b, and updates the bond type of the bond a having a larger electron density from the single bond to the double bond.

FIGS. 18A to 18D illustrate an example of a force field table. After performing processing illustrated in FIGS. 9A to 17C to identify the atomic species of each atom in a target molecule, the identifying apparatus 101 refers to a force field table to assign force-field information corresponding to the atomic species. The force field table is a table in which spring constants and so on are stored for respective atomic species noted in the literature by Wendy D. Cornell et al. As the force field table, there are a bond parameter table 1801, a bond-angle parameter table 1802, a dihedral parameter table 1803, and a non-bond parameter table 1804.

The bond parameter table 1801 illustrated in FIG. 18A has records 1801-1 to 1801-5. The bond-angle parameter table 1802 illustrated in FIG. 18B also has records 1802-1 to 1802-4. In addition, the dihedral parameter table 1803 illustrated in FIG. 18C has records 1803-1 to 1803-4. Additionally, the non-bond parameter table 1804 illustrated in FIG. 18D has records 1804-1 to 1804-5.

"Rk", "Req", "Tk", "Teq", "Pk", "p", "n", "vdw", and "wd" fields in the bond parameter table 1801, the bond-angle parameter table 1802, the dihedral parameter table 1803, and the non-bond parameter table 1804 are described later with reference to FIG. 19. Each of the bond parameter table 1801, the bond-angle parameter table 1802, and the dihedral parameter table 1803 has a first field in which a combination of the atomic species is stored. Similarly, the non-bond parameter table 1804 has a first field in which an atomic species is stored.

For example, the record 1801-1 indicates that Rk is 290.1 and Req is 1.55 when the atom of atomic species [c] and the atom of atomic species [c] combine with each other.

FIG. 19 illustrates an example of a molecular force-field function. The identifying apparatus 101 assigns the values of the parameters assigned in FIGS. 18A to 18D to the function illustrated in FIG. 19 to calculate a molecular force field. In FIG. 19, the function for calculating a GAFF force field is depicted as equation (5). Equation (5) is noted in Junmei Wang, and three others, "Automatic atom type and bond type perception in molecular mechanical calculations", *Journal of Molecular Graphics and Modelling*, Vol. 25, pp. 247-260, 2006 and Hideaki Fujitani, and two others, "Massively parallel computation of absolute binding free energy with well-equilibrated states", *Physical Review E*, Vol. 79, 2009.

$$E = \sum_{bonds} k_r(r - r_{eq})^2 + \quad (5)$$

$$\sum_{angles} k_\theta(\theta - \theta_{eq})^2 + \sum_{dihedrals} \sum_n \frac{1}{2} v_n[1 + \cos(n\varphi - \gamma)] +$$

$$\sum_{i<j} 4\varepsilon_{ij}\left[\left(\frac{\sigma_{ij}}{r_{ij}}\right)^{12} - \left(\frac{\sigma_{ij}}{r_{ij}}\right)^6\right] + \sum_{i<j} \frac{q_i q_j}{r_{ij}}$$

Now, a description will be given of what are indicated by the elements in equation (5). The first term of equation (5) indicates an energy related to bonds. The second term of equation (5) indicates an energy related to bond angles. The third term in equation (5) indicates an energy related to dihedrals. The fourth term in equation (5) indicates an energy related to non-bonds. The fifth term in equation (5) indicates an energy related to charges.

Next, a description will be given of variables that appear in equation (5). In this case, $k_r$, $k_\theta$, and $v_n$ are constants for the force field. Also, $k_r$ corresponds to Rk in the bond parameter table 1801. In addition, $k_\theta$ corresponds to Tk in the bond-angle parameter table 1802. Similarly, $v_n$ corresponds to Pk in the dihedral parameter table 1803.

Also, r indicates the distance between two atoms, $r_{eq}$ indicates an equilibrium distance between two atoms, and also $r_{eq}$ corresponds to Req in the bond parameter table 1801.

In addition, θ indicates a bond angle, and $\theta_{eq}$ indicates an equilibrium bond angle. The equilibrium bond angle has the value of the most stable bond angle. In addition, $\theta_{eq}$ corresponds to Teq in the bond-angle parameter table 1802.

Also, φ indicates a dihedral, n is a value used for a program, and n corresponds to n in the dihedral parameter table 1803. For example, for the records 1803-1 and 1803-2, processing when n in [n]-[c3]-[c]-[n] is 1 to 2 is performed. When n is a negative value, this indicates that there is a next record. In addition, γ indicates a phase and corresponds to p in the dihedral parameter table 1803.

In addition, i and j are identification numbers given to atoms. Also $\varepsilon_{ij}$ is a square root of a value resulting from multiplication of the value of wd for the atomic species of an atom with the identification number i and the value of wd for the atomic species of an atom with the identification number j, the values of wd being included in the non-bond parameter table 1804. Also, $\sigma_{ij}$ is the sum of the value of vdw for the atomic species of the atom with the identification number i and the value of vdw for the atomic specifies of the atom with the identification number j, the values of vdw being included in the non-bond parameter table 1804. In addition $r_{ij}$ is the distance between the atom with the identification number i and the atom with the identification number j in the non-bond parameter table 1804.

Also $q_i$ is the charge of the atom with the identification number i, and $q_j$ is the charge of the atom with the identification number j. Next, an example of processing for assigning a molecular force field will be described with reference to the flowcharts illustrated in FIGS. 20 to 25.

Figure 20:
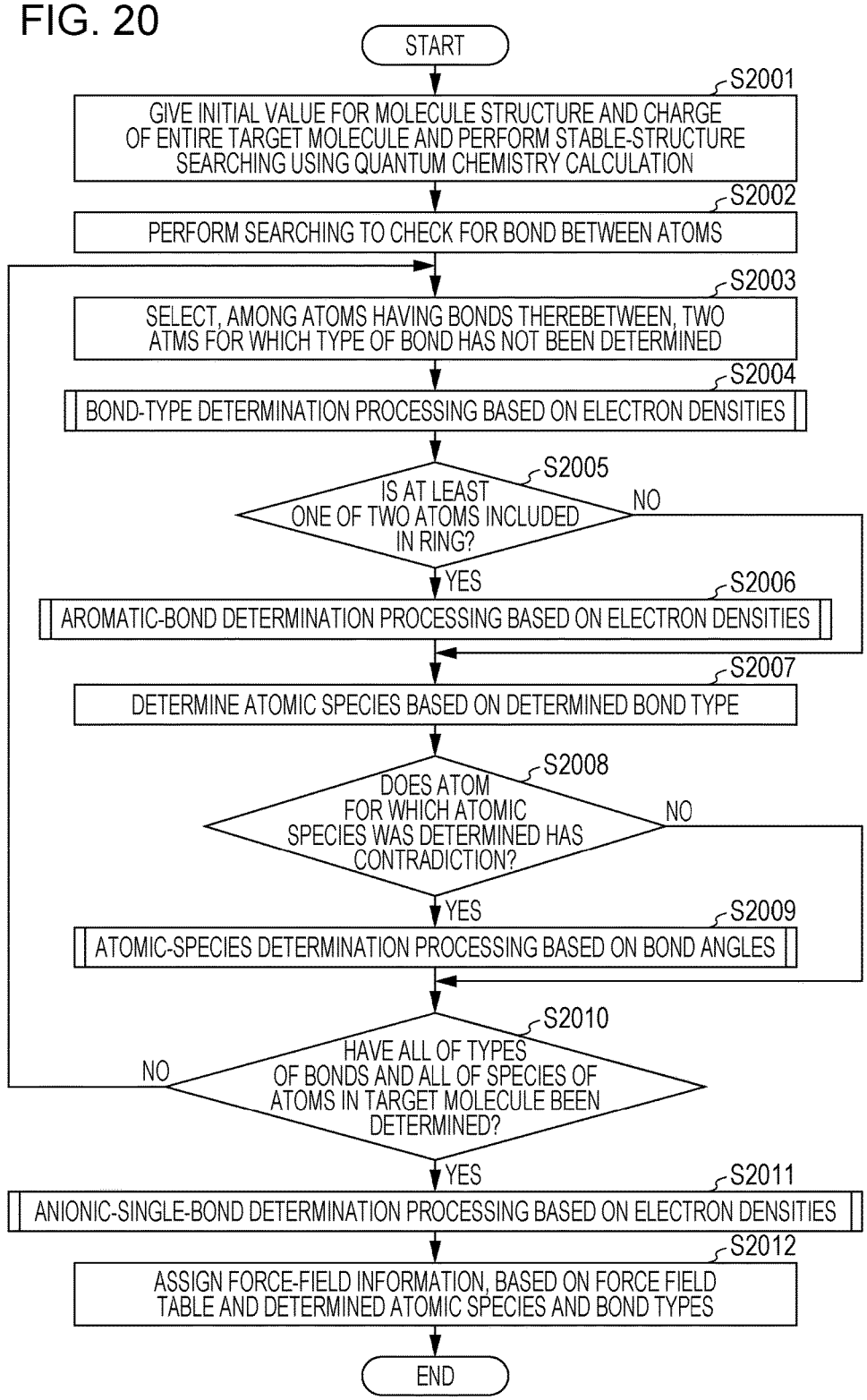
FIG. 20 is a flowchart illustrating an example of a procedure of processing for assigning a molecular force field.

FIG. 20 is a flowchart illustrating an example of a procedure of processing for assigning a molecular force field. The molecular force field assignment processing is processing for assigning a force field to a new molecule. The identifying apparatus 101 gives an initial value for a molecule structure and the charge of an entire target molecule and performs stable-structure searching using quantum-mechanical-calculation (step S2001). The stable-structure searching yields a density matrix P of electrons and an overlap integral matrix S of atomic orbitals. Next, the identifying apparatus 101 performs searching to check for a bond between atoms (step S2002). Subsequently, the identifying apparatus 101 selects, among atoms having bonds therebetween, two atoms for which the type of bond has not been determined (step S2003). Next, the identifying apparatus 101 executes bond-type determination processing based on electron densities (step S2004). Details of the bond-type determination processing based on electron densities are described later with reference to FIG. 21. After step S2004, the identifying apparatus 101 decides whether or not at least one of the two atoms is included in a ring (step S2005).

When at least one of the two atoms is included in a ring (YES in step S2005), the identifying apparatus 101 executes aromatic-bond determination processing based on electron densities (step S2006). Details of the aromatic-bond determination processing based on electron densities are described later with reference to FIG. 22. After executing step S2006 or when one of the two atoms is not included in a ring (NO in step S2005), the identifying apparatus 101 determines an atomic species based on the determined bond type (step S2007).

Subsequently, the identifying apparatus 101 decides whether or not the atom for which the atomic species was determined has a contradiction (step S2008). A case in which the atom has a contradiction is, for example, a case in which a valence of an atom for which the atomic species is determined and the number of bonds do not match each other.

When the atom for which the atomic species was determined has a contradiction (YES in step S2008), the identifying apparatus 101 executes atomic-species determination processing based on bond angles (step S2009). The atomic-species determination processing based on bond angles is described below with reference to FIGS. 24 and 25. After completing the process in step S2009 or when the atom for which the atomic species was determined has no contradiction (NO in step S2008), the identifying apparatus 101 decides whether or not all of the types of bonds and all of the species of atoms in the target molecule have been determined (step S2010). When there is any undetermined bond type or atom specifies (NO in step S2010), the process of the identifying apparatus 101 returns to step S2003.

When all of the types of the bonds and the species of the atoms are determined (YES in step S2010), the identifying apparatus 101 executes anionic-single-bond determination processing based on electron densities (step S2011). Details of the anionic-single-bond determination processing based on electron densities are described later with reference to FIG. 23. The anionic-single-bond determination processing based on electron densities is processing for performing searching to determine whether or not there is a single bond having an anionic atom. The single bond having an anionic atom is defined with an AM1BCC charge and is not defined with a GAFF force field. Thus, when a GAFF force field is used, the identifying apparatus 101 may omit the execution of the process in step S2011.

After executing step S2011, the identifying apparatus 101 assigns force-field information, based on the force field table and the determined atomic species and bond types (step S2012). For example, the identifying apparatus 101 may output the determined atomic species and bond types to another apparatus as a specific process in step S2012. After the outputting, the other apparatus assigns force-field information corresponding to the determined atomic species and bond types. After completing step S2012, the identifying apparatus 101 ends the molecular-force-field assignment processing. By executing the molecular-force-field assignment processing, the identifying apparatus 101 can assign an appropriate force field to a new molecule.

In FIG. 20, the identifying apparatus 101 performs the atomic-species determination processing based on bond angles, when the atom for which the atomic species was determined has a contradiction. As another method, the identifying apparatus 101 may also determine the atomic species by selecting a reliable method for each atom from among the method for the atomic-species determination based on valences, the method for the atomic-species determination based on bond distances, the method for the atomic-species determination based on electron densities, and the method for the atomic-species determination based on bond angles. For example, the identifying apparatus 101 performs the method for the atomic-species determination based on valences with respect to hydrogen atoms and performs the method for the atomic-species determination based on bond angles with respect to nitrogen atoms.

Figure 21:
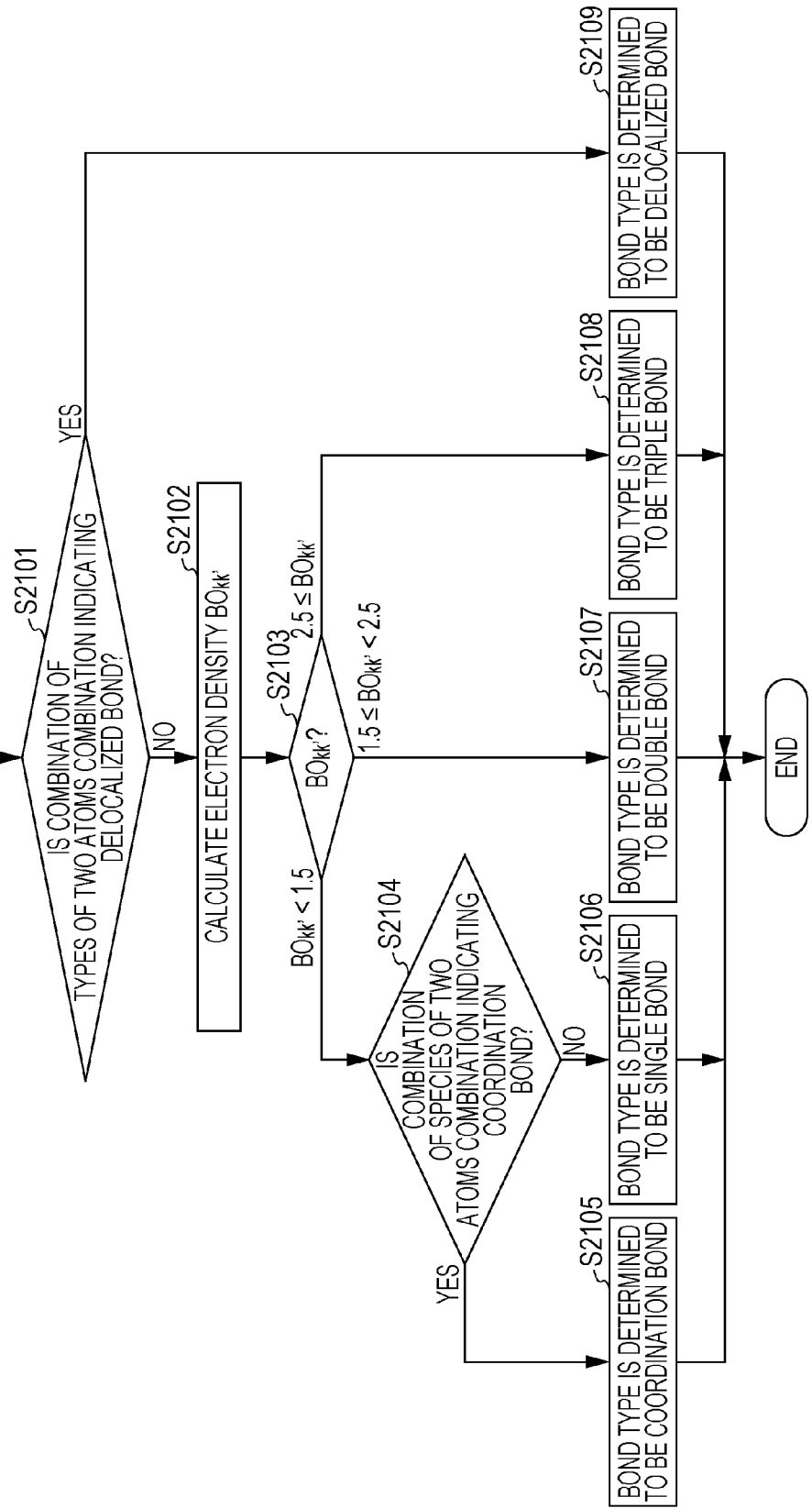
FIG. 21 is a flowchart illustrating an example of a procedure of bond-type determination processing based on electron densities.

FIG. 21 is a flowchart illustrating an example of a procedure of the bond-type determination processing based on electron densities. The bond-type determination processing based on electron densities is processing for determining the type of bond by using electron densities. The identifying apparatus 101 decides whether or not a combination of the types of two atoms is a combination indicating a delocalized bond (step S2101). When the combination of the types of two atoms is not a combination indicating a delocalized bond (NO in step S2101), the identifying apparatus 101 calculates an electron density $BO_{kk'}$ (step S2102). The amount of processing for calculating the electron density $BO_{kk'}$ in the process in step S2102 is negligibly small relative to the amount of processing performed in step S2101, since the density matrix P of electrons and the overlap integral matrix S of atomic orbitals are determined in the process in step S2101.

After step S2102, the identifying apparatus 101 checks the electron density $BO_{kk'}$ between the two atoms (step S2103). When $BO_{kk'}$ is smaller than 1.5 (step S2103: $BO_{kk'}<1.5$), the identifying apparatus 101 decides whether or not the combination of the species of the two atoms is a combination indicating a coordination bond (step S2104). In the process in step S2104, the coordination bond is defined with an AM1BCC charge and is not defined with a GAFF force field. Hence, when the GAFF force field is used, the identifying apparatus 101 does not perform the process in step S2104, and the process proceeds to step S2106. When the combination of the species of the two atoms is a combination indicating a coordination bond (YES in step S2104), the identifying apparatus 101 determines that the bond type is a coordination bond (step S2105).

When the combination of the species of the two atoms is not a combination indicating a coordination bond (NO in step S2104), the identifying apparatus 101 determines that bond type is a single bond (step S2106). When $BO_{kk'}$ is 1.5 or larger and is smaller than 2.5 (step S2103: $1.5 \leq BO_{kk'}<2.5$), the identifying apparatus 101 determines that the bond type is a double bond (step S2107). When $BO_{kk'}$ is 2.5 or larger (step S2103: $2.5 \leq BO_{kk'}$), the identifying apparatus 101 determines that the bond type is a triple bond (step S2108). When the combination of the types of the two atoms is a combination indicating a delocalized bond (YES in step S2101), the identifying apparatus 101 determines that the bond type is a delocalized bond (step S2109). After completing one of the processes in steps S2105 to S2109, the identifying apparatus 101 ends the bond-type determination processing based on electron densities. By executing the bond-type determination processing based on electron densities, the identifying apparatus 101 can determine an appropriate type of bond.

Figure 22:
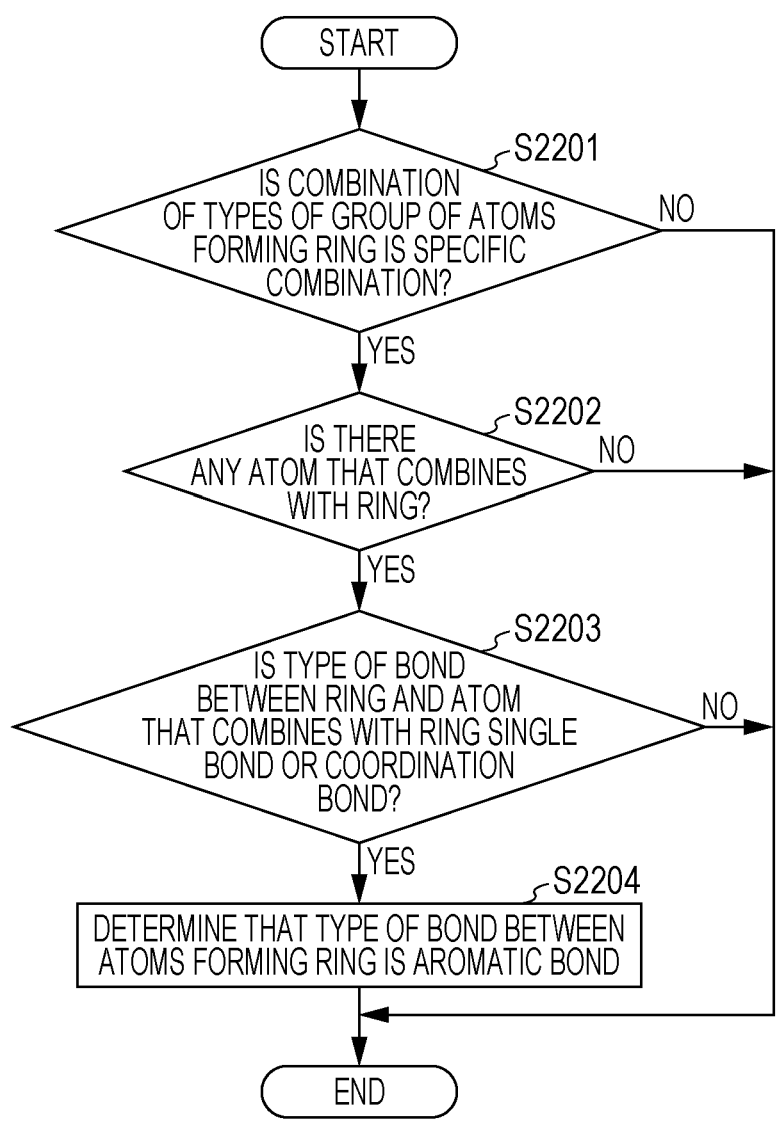
FIG. 22 is a flowchart illustrating an example of a procedure of the aromatic-bond determination procedure based on electron densities.

FIG. 22 is a flowchart illustrating an example of a procedure of aromatic-bond determination processing based on an electron density. The aromatic-bond determination processing based on electron densities is processing for determining that the type of bond is an aromatic bond by using an electron density. The identifying apparatus 101 decides whether or not a combination of the types of a group of atoms forming a ring is a specific combination (step S2201). When the combination is a specific combination (YES in step S2201), the identifying apparatus 101 decides whether or not there is any atom that combines with the ring (step S2202). When there is an atom that combines with the ring (YES in step S2202), the identifying apparatus 101 decides whether or not the type of bond between the ring and the atom that combines with the ring is a single bond or a coordination bond (step S2203). When the type of bond is a single bond or a coordination bond (YES in step S2203), the identifying apparatus 101 determines that the type of bond between the atoms forming the ring is an aromatic bond (step S2204).

After completing step S2204, when the combination in question is not a specific combination (NO in step S2201), when there is not any atom that combines with the ring (NO in step S2202), or when the type of bond is a type other than a single bond or a coordination bond (NO in step S2203), the identifying apparatus 101 ends the aromatic-bond determination processing based on electron densities. By executing the aromatic-bond determination processing based on electron densities, the identifying apparatus 101 can determine an appropriate type of bond for the group of atoms that combine via the aromatic bonds.

Figure 23:
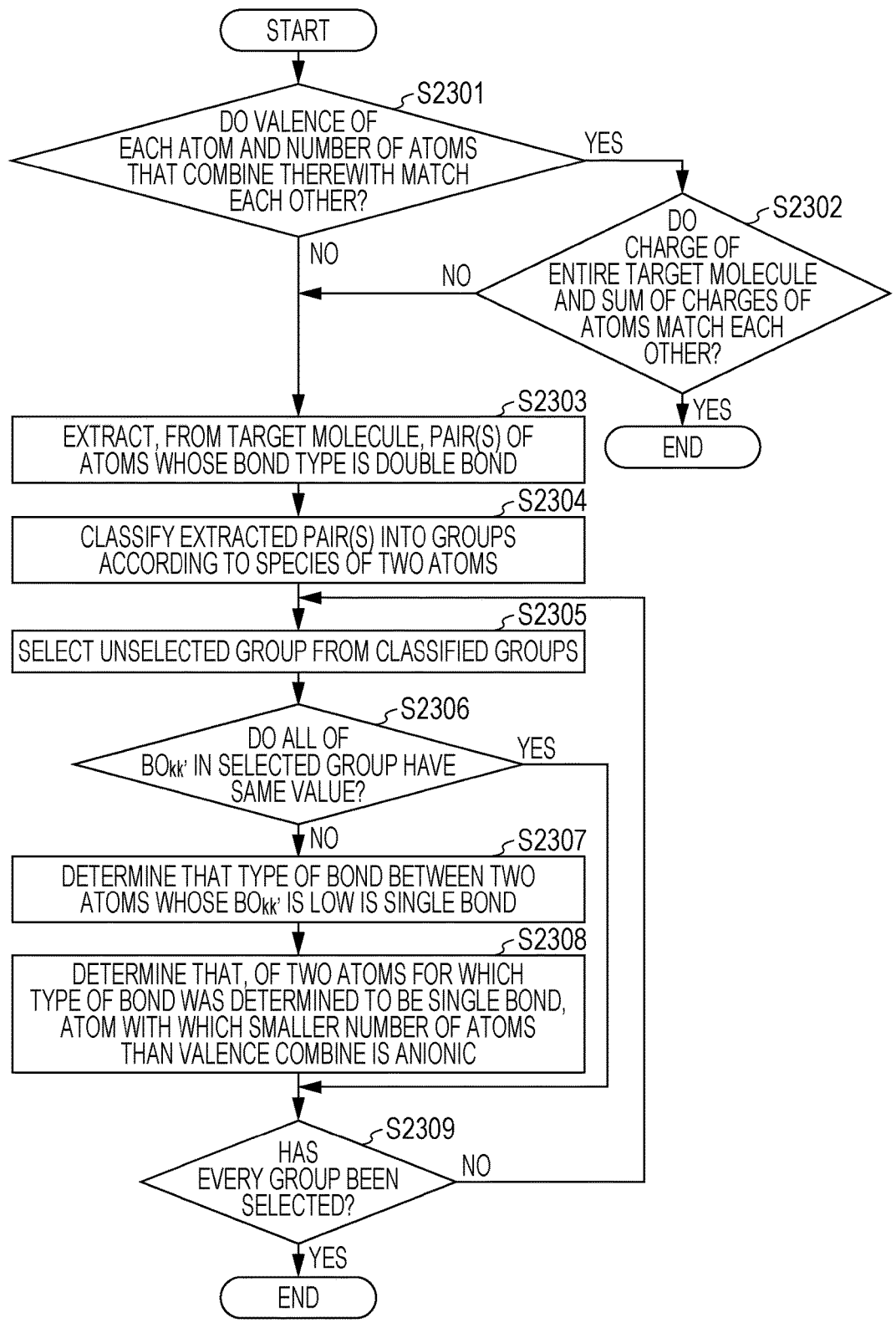
FIG. 23 is a flowchart illustrating an example of a procedure of anionic-single-bond determination processing based on electron densities.

FIG. 23 is a flowchart illustrating an example of a procedure of anionic-single-bond determination processing based on electron densities. The anionic-single-bond determination processing based on electron densities is processing in which a type of bond that is likely to be a single bond including an anionic atom is searched for using electron densities and the found type of bond is determined to be a single bond including an anionic atom when a condition is satisfied. The identifying apparatus 101 decides, for each atom, whether or not the valence thereof and the number of atoms that combine with the atom match each other (step S2301). When the valence and the number of atoms that combine do not match each other (YES in step S2301), the identifying apparatus 101 decides whether or not the charge of the entire target molecule and the sum of the charges of the atoms match each other (step S2302). When the charge of the entire target molecule and the sum of the charges of the atoms match each other (YES in step S2302), the identifying apparatus 101 ends the anionic-single-bond determination processing based on electron densities.

When the valence and the number of atoms that combine do not match each other (NO in step S2301) or when the charge of the entire target molecule and the sum of the charges of the atoms do not match each other (NO in step S2302), the identifying apparatus 101 extracts, from the target molecule, a pair or pairs of atoms whose bond type is a double bond (step S2303). Subsequently, the identifying apparatus 101 classifies the extracted pair(s) into groups according to the species of two atoms (step S2304). Next, the identifying apparatus 101 selects an unselected group from the classified groups (step S2305). When the number of combinations included in the selected group is one, the process of the identifying apparatus 101 proceeds to process in step S2309 described below. After step S2305, the identifying apparatus 101 decides whether or not all of $BO_{kk'}$ in the selected group have the same value (step S2306).

When all of $BO_{kk'}$ do not have the same value (NO in step S2306), the identifying apparatus 101 determines that the type of bond between two atoms whose $BO_{kk'}$ is low is a single bond (step S2307). In addition, the identifying apparatus 101 determines that, of the two atoms for which the type of bond was determined to be a single bond, the atom with which a smaller number of atoms than the valence combine is anionic (step S2308).

After completing the process in step S2308 or when all of the bond orders $BO_{kk'}$ in the selected group have the same value (YES in step S2306), the identifying apparatus 101 decides whether or not every group has been selected (step S2309). When there is any unselected group (NO in step S2309), the process of the identifying apparatus 101 returns to step S2305. When every group has been selected (YES in step S2309), the identifying apparatus 101 ends the anionic-single-bond determination processing based on electron densities. By executing the anionic-single-bond determination processing based on electron densities, the identifying apparatus 101 can determine a more correct type of bond and thus can assign a more accurate molecular force field.

Figure 24:
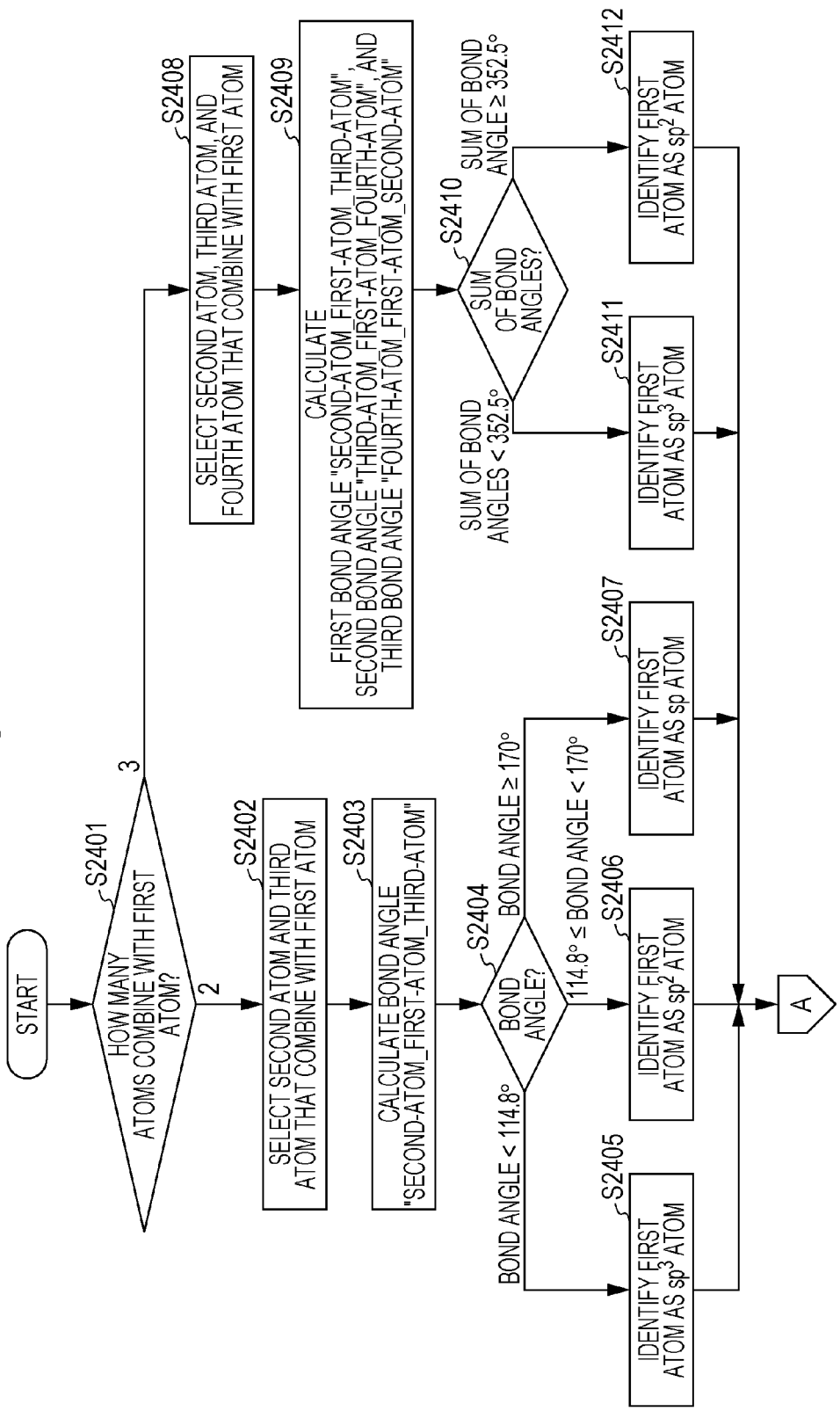
FIG. 24 is a flowchart (part 1) illustrating an example of a procedure of atomic-species determination processing based on bond angles.
Figure 25:
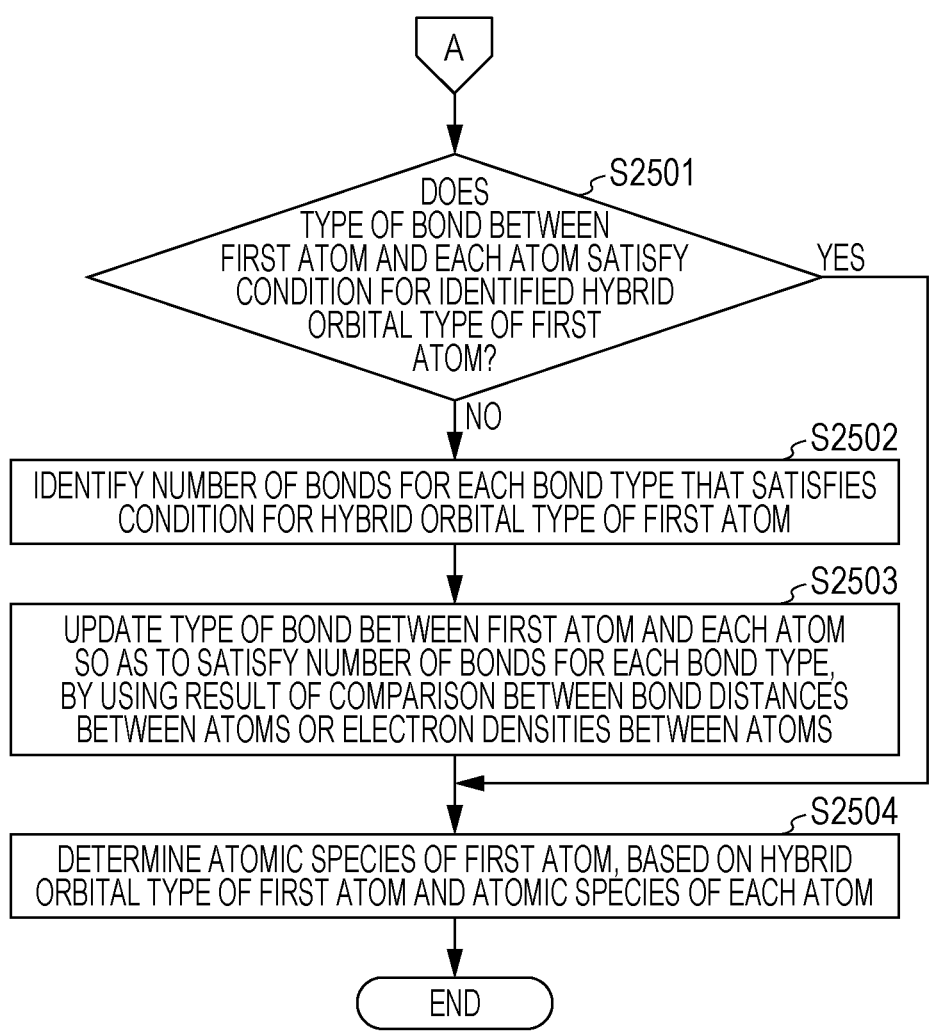
FIG. 25 is a flowchart (part 2) illustrating an example of the procedure of the atomic-species determination processing based on bond angles.

FIG. 24 is a flowchart (part 1) illustrating an example of a procedure of the atomic-species determination processing based on bond angles. FIG. 25 is a flowchart (part 2) illustrating an example of the procedure of the atomic-species determination processing based on bond angles. The atomic-species determination processing based on bond angles is processing for determining an atomic species by using bond angles. A first atom in FIGS. 24 and 25 corresponds to the atom having a contradiction in step S2008.

The identifying apparatus 101 decides whether the number of atoms that combine with a first atom is "2" or "3" (step S2401). When the number of atoms that combine with the first atom is "1", no bond angle is formed, and thus processing illustrated in FIGS. 24 and 25 ends. When the number of atoms that combine with the first atom is two (step S2401: "2"), the identifying apparatus 101 selects a second atom and a third atom that combine with the first atom (step S2402). Next, by using the position information, the identifying apparatus 101 calculates a bond angle "second-atom_first-atom_third-atom" (step S2403). An arithmetic operation using an elementary function may be used as a method for determining a bond angle based on the position information.

After S2403, the identifying apparatus 101 decides to which of certain conditions the bond angle corresponds (step S2404). Next, a description will be given of a case in which the third decision method described above with reference to FIG. 5 is described as the certain conditions.

When the bond angle is less than 114.8° (step S2404: bond angle<114.8°), the identifying apparatus 101 identifies the first atom as an $sp^3$ atom (step S2405). When the bond angle is a 114.8° or more and is less than 170° (step S2404: 114.8°≤ bond angle<170°), the identifying apparatus 101 identifies the first atom as an $sp^2$ atom (step S2406). In addition, when the bond angle is 170° or more (step S2404: the bond angle≥170°), the identifying apparatus 101 identifies the first atom as an sp atom (step S2407).

When the number of atoms that combine with the first atom is three (step S2401: "3"), the identifying apparatus 101 selects a second atom, a third atom, and a fourth atom that combine with the first atom (step S2408). Next, the identifying apparatus 101 calculates a first bond angle "second-atom_first-atom_third-atom", a second bond angle "third-atom_first-atom_fourth-atom" and a third bond angle "fourth-atom_first-atom_second-atom" (step S2409). Subsequently, the identifying apparatus 101 decides which of conditions described below the sum of the first bond angle, the second bond angle, and the third bond angle matches (step S2410). The conditions will be described in conjunction with a case in which the fourth decision method described above and illustrated in FIG. 5.

When the sum of the bond angles is less than 352.5° (step S2410: the sum of the bond angles<352.5°), the identifying apparatus 101 identifies the first atom as an $sp^3$ atom (step S2411). When the sum of the bond angles is larger than or equal to 352.5° (step S2410: the sum of the bond angle is) 352.5°, the identifying apparatus 101 identifies the first atom as an $sp^2$ atom (step S2412).

After executing one of the processes in steps S2405, S2406, S2407, S2411, and S2412, the identifying apparatus 101 executes a process in step S2501 illustrated in FIG. 25.

Referring to FIG. 25, the identifying apparatus 101 decides whether or not the type of bond between the first atom and each of the atoms that combine with the first atom satisfies the condition for the identified hybrid orbital type of the first atom (step S2501).

When the type of bond does not satisfy the condition for the identified hybrid orbital type of the first atom (NO in step S2501), the identifying apparatus 101 identifies the number of bonds for each type of bond so that the number satisfies the condition for the identified hybrid orbital type of the first atom (step S2502). The identifying apparatus 101 identifies the number of bonds for each type of bond by referring to the bond-type condition table 313. For example, when the first atom is an sp atom and the valence is 3, the first atom has one triple bond or has one double bond and one single bond. Also, when the first atom is an $sp^2$ atom and the valence is 3, the first atom has two double bonds and one single bond. In addition, when the first atom is an sp atom and the valence is 3, the first atom has three single bonds.

Next, by using a result of comparison between the bond distances between the atoms or the electron densities between the atoms, the identifying apparatus 101 updates the type of bond between the first atom and each atom so as to satisfy the number of bonds for each bond type (step S2503). After the process in step S2503 is completed or when the condition for the identified hybrid orbital type of the first atom is satisfied (YES in step S2501), the identifying apparatus 101 determines the atomic species of the first atom, based on the hybrid orbital type of the first atom and the atomic species of each atom (step S2504). After completing the process in step S2504, the identifying apparatus 101 ends the atomic-species determination processing based on bond angles. By executing the atomic-species determination processing based on bond angles, the identifying apparatus 101 can improve the determination accuracy more than that of any of the method for determining the type of bond by using valences, the method for determining the type of bond based on the bond distance between atoms, and the method for determining the type of bond based on the electron density between atoms.

As described above, by utilizing the fact that the bond angle increases according to the hybrid orbital of an atom, the identifying apparatus 101 identifies the hybrid orbital of an atom based on bond angles obtained by quantum-mechanical-calculation. With this arrangement, the identifying apparatus 101 can identify the hybrid orbital with high accuracy even if the calculation accuracy of the quantum-mechanical-calculation is low and can also improve the accuracy of assigning a molecular force field.

In addition, based on the condition stored in the bond-angle condition table 312, the identifying apparatus 101 may identify the hybrid orbital type of the first atom as the hybrid orbital type corresponding to the condition satisfied by the sum of bond angles. With this arrangement, the identifying apparatus 101 utilizes $sp^2$ atoms lying on substantially the same flat surface, it is possible to perform high-accuracy decision as to whether or not the atom in question is an $sp^2$ atom or an $sp^3$ atom.

The identifying apparatus 101 may also refer to the bond-type condition table 313 to decide whether or not the type of bond between atoms satisfies the condition for the identified hybrid orbital type of the first atom. Such an arrangement allows the identifying apparatus 101 to improve the accuracy of determining the bond type determined by using any of the method for bond-type determination using valences, the method for bond-type determination based on the bond distance between atoms, and the method for the bond-type determination based on the electron density between atoms. The identifying apparatus 101 may also output the identification information of the first atom, the identification information being obtained when it was decided that the condition is not satisfied. The user of the identifying apparatus 101 may also view an output result and modify the type of bond based on the experience of the user of the identifying apparatus 101. The identifying apparatus 101 may also execute another method that has not been executed among the method for determining the type of bond by using valences, the method for determining the type of bond based on the bond distance between atoms, and the method for determining the type of bond based on the electron density between atoms.

In addition, upon deciding that the condition is not satisfied, the identifying apparatus 101 may update the type of bond between the first atom and each of the atoms, based on the condition for the hybrid orbital type of the first atom and the result of comparison between the distances or the electron densities between the atoms. Such an arrangement allows the identifying apparatus 101 to improve the accuracy of determining the bond type determined by using any of the method for bond-type determination using valences, the method for bond-type determination based on the bond distance between atoms, and the method for the bond-type determination based on the electron density between atoms. In addition, the identifying apparatus 101 can also correctly determine the type of bond that is not correctly determined by any of the method for determining the type of bond by using valences, the method for determining the type of bond based on the bond distance between atoms, and the method for determining the type of bond based on the electron density between atoms.

The identifying apparatus 101 may also determine the atomic species of the first atom, based on the identified hybrid orbital type of the first atom and the atomic species of each of the atoms that combine with the first atom. In the method for determining the type of bond by using valences, the method for determining the type of bond based on the bond distance between atoms, or the method for determining the type of bond based on the electron density between atoms, the type of bond is identified and the corresponding atomic species is identified. However, the type of bond may or may not be determined in the present embodiment.

The identifying apparatus 101 may also execute the decision in conjunction with at least one of the method for determining the type of bond by using valences, the method for determining the type of bond based on the bond distance between atoms, and the method for determining the type of bond based on the electron density between atoms, it is possible to achieve high accuracy and high efficiency. In addition, since the bond angle can easily be determined using an elementary function, such as a cosine formula, the amount of calculation is negligibly small relative to the quantum-mechanical-calculation.

A computer, such as a personal computer or a workstation, may be used to execute a prepared identifying program to realize the identifying method described in the present embodiment. The identifying program is recorded to a computer-readable recording medium, such as a hard disk, a flexible disk, a compact disc read only memory (CD-ROM), a magneto-optical (MO) disk, or a digital versatile disc (DVD), is subsequently read therefrom, and is executed by the computer. The identifying program may also be distributed over a network, such as the Internet.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. A non-transitory computer-readable storage medium storing an identifying program that causes a computer to execute a process, the process comprising:
   selecting, from a molecule in a structurally stable state, a second atom and a third atom that combine with a first atom;
   calculating a first angle between a first straight line passing through the first atom and the selected second atom and a second straight line passing through the first atom and the selected third atom, by referring to a first storage unit in which position information of each atom in the molecule is stored;
   identifying a hybrid orbital type of the first atom based on the calculated first angle, by referring to a second storage unit which stores a condition satisfied by a bond angle formed by the atom and two atoms that combine with the atom being stored in the second storage unit in association with a hybrid atomic orbital type;
   determining the atomic species of the first atom based on the identified hybrid orbital type of the first atom and the atomic species of each of the atoms that combine with the first atom;
   determining a molecular force field to assign to the molecule based on the atomic species; and
   simulating how a drug candidate substance reacts with proteins or viruses by utilizing the determined molecular force field, wherein
   a condition satisfied by a sum of bond angles formed by the atom and two atoms selected from three atoms that combine with the atom is stored in the second storage unit in association with a hybrid atomic orbital type; wherein
   when three atoms combine with the first atom, the selecting further selects, from the molecule, a fourth atom that combines with the first atom; wherein
   the calculating calculates a second angle between the first straight line and a third straight line passing through the first atom and the selected fourth atom and a third angle between the second straight line and the third straight line, by referring to the first storage unit; and wherein
   the identifying identifies the hybrid orbital type of the first atom by referring to the second storage unit and based on a sum of the first angle, the calculated second angle, and the calculated third angle.

2. The non-transitory computer-readable storage medium according to claim 1,
   wherein a condition satisfied by a bond type representing a bond between the atom and another atom that combines with the atom is further stored in the second storage unit in association with the hybrid orbital type of the atom; and
   the identifying program causes the computer to decide whether or not the type of bond between the first atom and each of the atoms that combine with the first atom satisfies a condition for the identified hybrid orbital type of the first atom, by referring to the second storage unit.

3. The non-transitory computer-readable storage medium according to claim 2,
   wherein the identifying program causes the computer to update, upon deciding that the type of bond between the first atom and each of the atoms does not satisfy the condition for the hybrid orbital type of the first atom, the type of bond between the first atom and each of the atoms, based on a condition for the hybrid orbital type of the first atom and a result of comparison between distances and electron densities between the first atom and the atoms.

4. The non-transitory computer-readable storage medium according to claim 1, further comprising simulating a geometric structure of the drug candidate substance.

5. The non-transitory computer-readable storage medium according to claim 1, further comprising simulating an electronic property of the drug candidate substance.

6. The non-transitory computer-readable storage medium according to claim 1, further comprising simulating a parameter of the drug candidate substance.

7. An identifying method executed by a computer, the identifying method comprising:
   selecting, from a molecule in a structurally stable state, a second atom and a third atom that combine with a first atom;
   calculating a first angle between a first straight line passing through the first atom and the selected second atom and a second straight line passing through the first atom and the selected third atom, by referring to a first storage unit in which position information of each atom in the molecule is stored;
   identifying a hybrid orbital type of the first atom based on the calculated first angle, by referring to a second storage unit which stores a condition satisfied by a bond angle formed by the atom and two atoms that combine with the atom being stored in the second storage unit in association with a hybrid atomic orbital type;
   determining the atomic species of the first atom based on the identified hybrid orbital type of the first atom and the atomic species of each of the atoms that combine with the first atom;
   determining a molecular force field to assign to the molecule based on the atomic species; and
   simulating how a drug candidate substance reacts with proteins or viruses by utilizing the determined molecular force field, wherein
   a condition satisfied by a sum of bond angles formed by the atom and two atoms selected from three atoms that combine with the atom is stored in the second storage unit in association with a hybrid atomic orbital type; wherein
   when three atoms combine with the first atom, the selecting further selects, from the molecule, a fourth atom that combines with the first atom; wherein
   the calculating calculates a second angle between the first straight line and a third straight line passing through the first atom and the selected fourth atom and a third angle between the second straight line and the third straight line, by referring to the first storage unit; and wherein
   the identifying identifies the hybrid orbital type of the first atom by referring to the second storage unit and based on a sum of the first angle, the calculated second angle, and the calculated third angle.

8. The identifying method according to claim 7,
   wherein a condition satisfied by a bond type representing a bond between the atom and another atom that combines with the atom is further stored in the second storage unit in association with the hybrid orbital type of the atom; and
   the identifying program causes the computer to decide whether or not the type of bond between the first atom and each of the atoms that combine with the first atom satisfies a condition for the identified hybrid orbital type of the first atom, by referring to the second storage unit.

9. The identifying method according to claim 8,
wherein the identifying program causes the computer to update, upon deciding that the type of bond between the first atom and each of the atoms does not satisfy the condition for the hybrid orbital type of the first atom, the type of bond between the first atom and each of the atoms, based on a condition for the hybrid orbital type of the first atom and a result of comparison between distances and electron densities between the first atom and the atoms.

10. The identifying method according to claim 7, further comprising simulating a geometric structure of the drug candidate substance.

11. The identifying method according to claim 7, further comprising simulating an electronic property of the drug candidate substance.

12. The identifying method according to claim 7, further comprising simulating a parameter of the drug candidate substance.

13. An identifying apparatus comprising:
a first storage unit;
a second storage unit; and
a processor coupled to the first and second storage units and configured to:
select, from a molecule in a structurally stable state, a second atom and a third atom that combine with a first atom;
calculate a first angle between a first straight line passing through the first atom and the second atom and a second straight line passing through the first atom and the third atom, by referring to the first storage unit in which position information of each atom in the molecule is stored;
identify a hybrid orbital type of the first atom based on the first angle, by referring to the second storage unit which stores a condition satisfied by a bond angle formed by the atom and two atoms that combine with the atom being stored in the second storage unit in association with a hybrid atomic orbital type;
determine the atomic species of the first atom based on the identified hybrid orbital type of the first atom and the atomic species of each of the atoms that combine with the first atom;
determine a molecular force field to assign to the molecule based on the atomic species; and
simulate how a drug candidate substance reacts with proteins or viruses by utilizing the determined molecular force field, wherein
a condition satisfied by a sum of bond angles formed by the atom and two atoms selected from three atoms that combine with the atom is stored in the second storage unit in association with a hybrid atomic orbital type; wherein
when three atoms combine with the first atom, the selecting further selects, from the molecule, a fourth atom that combines with the first atom; wherein
calculates a second angle between the first straight line and a third straight line passing through the first atom and the selected fourth atom and a third angle between the second straight line and the third straight line, by referring to the first storage unit; and wherein
identify the hybrid orbital type of the first atom by referring to the second storage unit and based on a sum of the first angle, the calculated second angle, and the calculated third angle.

14. The identifying apparatus according to claim 13,
wherein a condition satisfied by a bond type representing a bond between the atom and another atom that combines with the atom is further stored in the second storage unit in association with the hybrid orbital type of the atom; and
the processor further configured to decide whether or not the type of bond between the first atom and each of the atoms that combine with the first atom satisfies a condition for the identified hybrid orbital type of the first atom, by referring to the second storage unit.

15. The identifying apparatus according to claim 14, the processor further configured to:
update upon deciding that the type of bond between the first atom and each of the atoms does not satisfy the condition for the hybrid orbital type of the first atom, the type of bond between the first atom and each of the atoms, based on a condition for the hybrid orbital type of the first atom and a result of comparison between distances and electron densities between the first atom and the atoms.

16. The identifying apparatus according to claim 13, wherein the processor is further configured to simulate a geometric structure of the drug candidate substance.

17. The identifying apparatus according to claim 13, wherein the processor is further configured to simulate an electronic property of the drug candidate substance.

18. The identifying apparatus according to claim 13, wherein the processor is further configured to simulate a parameter of the drug candidate substance.

* * * * *